(12) United States Patent
Bhattacharyya

(10) Patent No.: US 7,943,825 B2
(45) Date of Patent: May 17, 2011

(54) METACASPASE II IN ENGINEERING SOYBEAN FOR DISEASE RESISTANCE

(75) Inventor: Madan K. Bhattacharyya, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 355 days.

(21) Appl. No.: 12/082,578

(22) Filed: Apr. 11, 2008

(65) Prior Publication Data
US 2009/0089894 A1    Apr. 2, 2009

Related U.S. Application Data

(60) Provisional application No. 60/911,342, filed on Apr. 12, 2007.

(51) Int. Cl.
    *A01H 1/00* (2006.01)
    *A01H 5/00* (2006.01)
    *C12N 15/09* (2006.01)
    *C12N 15/82* (2006.01)

(52) U.S. Cl. ........ 800/312; 800/279; 800/278; 800/298; 800/295; 435/69.1; 435/468; 435/415; 435/320.1; 536/23.2; 536/23.6

(58) Field of Classification Search .................. None
See application file for complete search history.

(56) References Cited

OTHER PUBLICATIONS

Romeis et al. The Plant Cell (1998), vol. 11, pp. 273-287.*
Gregory Martin. Current Opinion in Plant Biology (1999) 2:273-279.*
Uren, Anthony G. et al., "Identification of Paracaspases and Metacaspases:Two Ancient Families of Caspase-like Proteins, One of which Plays a Key Role in MALT Lymphoma", Molecular Cell, vol. 6, pp. 961-967, Oct. 2000.
Vercammen, Dominique et al., "Type II Metacaspases Atmc4 and Atmc9 of *Arabidopsis thaliana* Cleave Substrates after Arginine and Lysine", The Journal of Biological Chemistry, vol. 279, No. 44, pp. 45329-45336, Oct. 29, 2004.

* cited by examiner

*Primary Examiner* — Medina A Ibrahim
(74) *Attorney, Agent, or Firm* — McKee, Voorhees & Sease, P.L.C.

(57) ABSTRACT

The present invention is in the field of soybean genetics. More specifically, the invention relates to nucleic acid molecules from regions in the soybean genome, which are associated with soybean *Phytophthora* resistance. The invention also relates to methods of transforming soybean with constructs containing nucleic acid molecules encoding proteins for *Phytophthora* resistance, to produce modified or transgenic plants and plant cells having enhanced disease resistance.

21 Claims, 9 Drawing Sheets

Figure 4
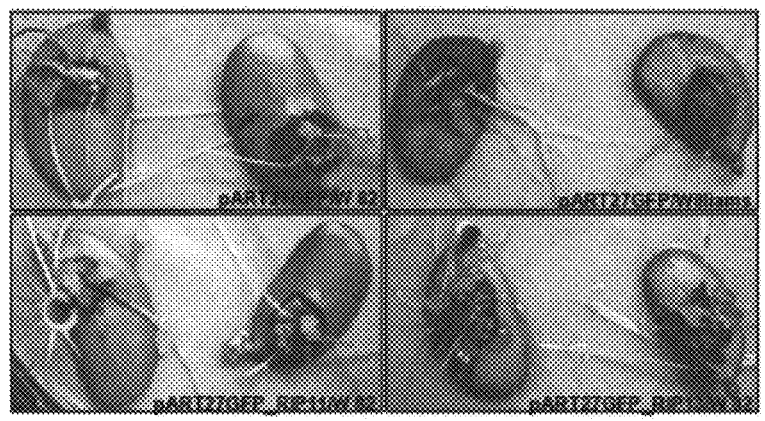
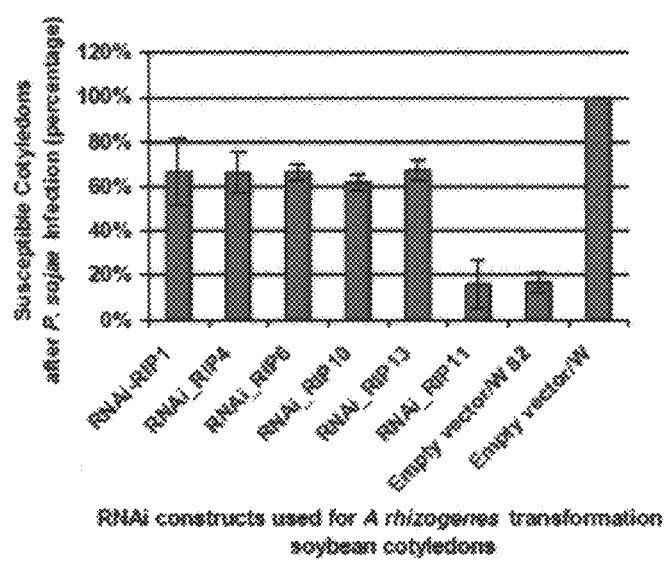
RNAi constructs used for A. rhizogenes transformation of soybean cotyledons

Figure 5

A  MAKKAVLIGINYPGTKAELKGCINDVWRMHRCLIDRYGFSEDDITVLID
TDESYTEPTGKNIRSALTRLIRSARPGDVLFVHYSGHGTRLPAETGEDD
DTGFDECIVPSDMNLITDDDFREFVDGVPRECKLTIVSDS[C]HSGGLIDG
AKEQIGTSTKGEGQQHSGSGSGFGLSSFLRRSVEDAIES[R]GVHIPSALR
HHRHKHEHEADDDRDIELPHVDHGYVKNRSLPLSTIIDILKQKTGKNDI
DVGKLRLSLYDIFGEDASPKVKKFM[K]VILNKLQQGDGGSGKQGGILGLV
GSLAQEFLKQKIDSSDDGGYAKPAMETKVESKYEAYAGTSSAKPRLSDG
GILMSGCQTDQTSADASPAGNSASAYGAFSNAIQAVIEESDGAVTNQEI
VLKAREKLKRGGFKQRPGLYCSDDHVDGPFVC  SEQ ID NO:1

B
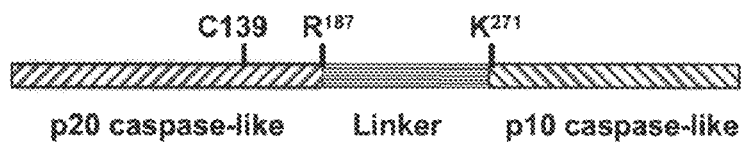

Figure 6

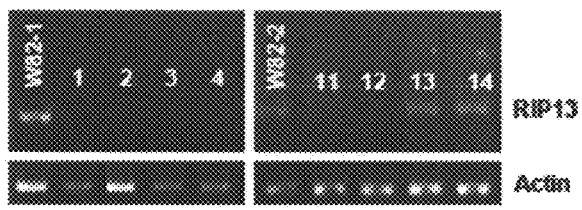

Figure 7

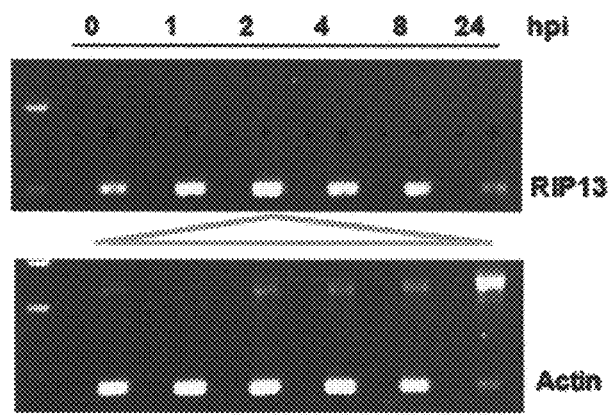

Figure 8

```
                                                                              SEQ ID NO:7
                                                                              SEQ ID NO:8
                                                                              SEQ ID NO:9 gi|81336192|gb|CO960058.1    MEQEDNTTIPTFTLRKFAEDQNNNN------SFTPSHKSLHVTRASRRRWR
gi|31306966|gb|CD392169.1    MEQEDNTTIPTFTLRKFAADQNNNNNNNN-SFTPSHKSLHVTRASRRRWR
RIPe                         MEQEDNTTIPTFTLRKFAADQNNNNNNNNSFTPSHKSLHVTRASRRRWR
                             **************.***      ****************** gi|81336192|gb|CO960058.1    KEVAVKDAVQEEDEDEKEEGEDGGDDREEIERKIHALQRIVFGGESLGVD
gi|31306966|gb|CD392169.1    KEVAVKEDEDVDE------------GDDREEIERKIHALQRIVFGGESLGVD
RIPe                         KEVAVKEDEDVDE------------GDDREEIERKIHALQRIVFGGESLGVD
                             ******:*:*:*             ************************* gi|81336192|gb|CO960058.1    KLFDETAGVILALQYQVKALRALGFTELEMEKTKFGG-
gi|31306966|gb|CD392169.1    KLFDETAGVILALQYQVKALRALGFTDKLEKETNFGGK
RIPe                         KLFDETAGVILALQYQVKALRALGFTDKLEKETNFGG-
                             **********************************:***
```

>GmMcII DNA Sequence (SEQ ID NO:1)
ATGGCGAAAAAAGCCGTTTTGATCGGAATAAACTACCCGGGAACAAAGGCGGAGCTGAAAGGATGCATAAACG
ACGTGTGGAGGATGCACCGCTGCCTCATCGATCGATACGGTTTCTCCGAAGACGACATCACCGTTTTGATCGA
CACGGACGAATCCTACACGGAGCCCACGGGGAAAAACATTCGGTCAGCGCTGACCAGACTCATACGATCGGCG
AGGCCGGGGGACGTGCTGTTCGTGCATTACAGCGGACATGGCACGCGCCTCCCCGCGGAAACCGGAGAGGATG
ATGACACTGGCTTTGATGAATGCATTGTTCCTTCTGATATGAACCTCATCACTGATGATGACTTCAGAGAATT
TGTAGATGGGGTCCCTAGAGAATGTAAGCTCACAATAGTATCAGATTCTTGCCATAGTGGTGGCCTAATTGAT
GGAGCTAAGGAGCAGATAGGAACTAGCACAAAGGGAGAAGGGCAACAACATTCTGGTTCTGGTTCTGGCTTTG
GATTATCCAGTTTTCTTCGTCGCTCCGTTGAGGACGCCATCGAATCTCGTGGAGTTCATATCCCTTCAGCATT
GCGCCATCATAGACACAAGCATGAACATGAAGCTGATGATGATAGGGACATTGAGCTTCCACATGTGGACCAT
GGCTATGTAAAGAATAGGTCATTGCCACTTTCTACCATCATAGACATACTCAAGCAGAAAACTGGGAAAAATG
ATATAGATGTTGGGAAATTGAGACTCTCGCTTTATGACATATTTGGGGAAGATGCTAGCCCTAAAGTGAAGAA
GTTCATGAAGGTTATCTTGAATAAACTCCAACAAGGGGATGGTGGAAGTGGAAAACAAGGTGGAATCTTGGGG
CTAGTGGGTAGTCTTGCCCAAGAGTTTCTCAAGCAAAAGATTGATTCAAGTGATGATGGTGGTTATGCAAAAC
CTGCCATGGAGACAAAGGTTGAAAGCAAATATGAGGCATATGCTGGAACAAGTTCAGCCAAGCCGCGCCTTTC
AGACGGCGGAATTCTGATGAGTGGTTGTCAAACAGACCAAACTTCTGCTGATGCAAGTCCAGCAGGTAACTCT
GCCAGTGCTTATGGAGCTTTTAGCAATGCAATACAGGCTGTGATTGAGGAGAGTGATGGTGCTGTCACAAATC
AAGAGATTGTTTTGAAGGCAAGGGAGAAGCTGAAGAGGGGAGGTTTCAAACAACGGCCAGGACTTTACTGCAG
TGATGACCATGTTGATGGTCCTTTTGTGTGCTGA >GmMcII Protein Sequence (SEQ ID NO:2)
MAKKAVLIGINYPGTKAELKGCINDVWRMHRCLIDRYGFSEDDITVLIDTDESYTEPTGK
NIRSALTRLIRSARPGDVLFVHYSGHGTRLPAETGEDDDTGFDECIVPSDMNLITDDDFR
EFVDGVPRECKLTIVSDSCHSGGLIDGAKEQIGTSTKGEGQQHSGSGSGFGLSSFLRRSV
EDAIESRGVHIPSALRHHRHKHEHEADDDRDIELPHVDHGYVKNRSLPLSTIIDILKQKT
GKNDIDVGKLRLSLYDIFGEDASPKVKKFMKVILNKLQQGDGGSGKQGGILGLVGSLAQE
FLKQKIDSSDDGGYAKPAMETKVESKYEAYAGTSSAKPRLSDGGILMSGCQTDQTSADAS
PAGNSASAYGAFSNAIQAVIEESDGAVTNQEIVLKAREKLKRGGFKQRPGLYCSDDRVDG
PFVC >GmMcII p10-like nucleotide sequence (SEQ ID NO:3)
AAGGTTATCTTGAATAAACTCCAACAAGGGGATGGTGGAAGTGGAAAACAAGGTGGAATCTTGGGGCTAGTGG
GTAGTCTTGCCCAAGAGTTTCTCAAGCAAAAGATTGATTCAAGTGATGATGGTGGTTATGCAAAACCTGCCAT
GGAGACAAAGGTTGAAAGCAAATATGAGGCATATGCTGGAACAAGTTCAGCCAAGCCGCGCCTTTCAGACGGC
GGAATTCTGATGAGTGGTTGTCAAACAGACCAAACTTCTGCTGATGCAAGTCCAGCAGGTAACTCTGCCAGTG
CTTATGGAGCTTTTAGCAATGCAATACAGGCTGTGATTGAGGAGAGTGATGGTGCTGTCACAAATCAAGAGAT
TGTTTTGAAGGCAAGGGAGAAGCTGAAGAGGGGAGGTTTCAAACAACGGCCAGGACTTTACTGCAGTGATGAC
CATGTTGATGGTCCTTTTGTGTGCTGA >>GmMcII p10-like amino acid sequence (SEQ ID NO:4)
RVILNKLQQGDGGSGKQGGILGLVGSLAQEFLKQKIDSSDDGGYAKPAMETKVESKYEAY
AGTSSAKPRLSDGGILMSGCQTDQTSADASPAGNSASAYGAFSNAIQAVIEESDGAVTNQ
EIVLKAREKLKRGGFKQRPGLYCSDDRVDGPFVC >GmMcII p20-like nucleotide sequence(SEQ ID NO:5)
ATGGCGAAAAAAGCCGTTTTGATCGGAATAAACTACCCGGGAACAAAGGCGGAGCTGAAAGGATGCATAAACG
ACGTGTGGAGGATGCACCGCTGCCTCATCGATCGATACGGTTTCTCCGAAGACGACATCACCGTTTTGATCGA
CACGGACGAATCCTACACGGAGCCCACGGGGAAAAACATTCGGTCAGCGCTGACCAGACTCATACGATCGGCG
AGGCCGGGGGACGTGCTGTTCGTGCATTACAGCGGACATGGCACGCGCCTCCCCGCGGAAACCGGAGAGGATG
ATGACACTGGCTTTGATGAATGCATTGTTCCTTCTGATATGAACCTCATCACTGATGATGACTTCAGAGAATT
TGTAGATGGGGTCCCTAGAGAATGTAAGCTCACAATAGTATCAGATTCTTGCCATAGTGGTGGCCTAATTGAT
GGAGCTAAGGAGCAGATAGGAACTAGCACAAAGGGAGAAGGGCAACAACATTCTGGTTCTGGTTCTGGCTTTG
GATTATCCAGTTTTCTTCGTCGCTCCGTTGAGGACGCCATCGAATCTCGT >GmMcII p20-like amino acid sequence (SEQ ID NO:6)
MAKKAVLIGINYPGTKAELKGCINDVWRMHRCLIDRYGFSEDDITVLIDTDESYTEPTGK
NIRSALTRLIRSARPGDVLFVHYSGHGTRLPAETGEDDDTGFDECIVPSDMNLITDDDFR
EFVDGVPRECKLTIVSDSCHSGGLIDGAKEQIGTSTKGEGQQHSGSGSGFGLSSFLRRSV
EDAIESR

Figure 12

SEQUENCE LISTING

<160> NUMBER OF SEQ ID NOS: 63

<210> SEQ ID NO 1
<211> LENGTH: 1275
<212> TYPE: DNA
<213> ORGANISM: Glycine max
<220> FEATURE:
<221> NAME/KEY: CDS
<222> LOCATION: (1)..(1275)
<223> OTHER INFORMATION:

<400> SEQUENCE: 1

```
atg gcg aaa aaa gcc gtt ttg atc gga ata aac tac ccg gga aca aag       48
Met Ala Lys Lys Ala Val Leu Ile Gly Ile Asn Tyr Pro Gly Thr Lys
1               5                   10                  15 gcg gag ctg aaa gga tgc ata aac gac gtg tgg agg atg cac cgc tgc       96
Ala Glu Leu Lys Gly Cys Ile Asn Asp Val Trp Arg Met His Arg Cys
                20                  25                  30 ctc atc gat cga tac ggt ttc tcc gaa gac gac atc acc gtt ttg atc      144
Leu Ile Asp Arg Tyr Gly Phe Ser Glu Asp Asp Ile Thr Val Leu Ile
            35                  40                  45 gac acg gac gaa tcc tac acg gag ccc acg ggg aaa aac att cgg tca      192
Asp Thr Asp Glu Ser Tyr Thr Glu Pro Thr Gly Lys Asn Ile Arg Ser
        50                  55                  60 gcg ctg acc aga ctc ata cga tcg gcg agg ccg ggg gac gtg ctg ttc      240
Ala Leu Thr Arg Leu Ile Arg Ser Ala Arg Pro Gly Asp Val Leu Phe
65                  70                  75                  80 gtg cat tac agc gga cat ggc acg cgc ctc ccc gcg gaa acc gga gag      288
Val His Tyr Ser Gly His Gly Thr Arg Leu Pro Ala Glu Thr Gly Glu
                85                  90                  95 gat gat gac act ggc ttt gat gaa tgc att gtt cct tct gat atg aac      336
Asp Asp Asp Thr Gly Phe Asp Glu Cys Ile Val Pro Ser Asp Met Asn
                100                 105                 110 ctc atc act gat gat gac ttc aga gaa ttt gta gat ggg gtc cct aga      384
Leu Ile Thr Asp Asp Asp Phe Arg Glu Phe Val Asp Gly Val Pro Arg
            115                 120                 125 gaa tgt aag ctc aca ata gta tca gat tct tgc cat agt ggt ggc cta      432
Glu Cys Lys Leu Thr Ile Val Ser Asp Ser Cys His Ser Gly Gly Leu
        130                 135                 140 att gat gga gct aag gag cag ata gga act agc aca aag gga gaa ggg      480
Ile Asp Gly Ala Lys Glu Gln Ile Gly Thr Ser Thr Lys Gly Glu Gly
145                 150                 155                 160 caa caa cat tct ggt tct ggt tct ggc ttt gga tta tcc agt ttt ctt      528
Gln Gln His Ser Gly Ser Gly Ser Gly Phe Gly Leu Ser Ser Phe Leu
                165                 170                 175 cgt cgc tcc gtt gag gac gcc atc gaa tct cgt gga gtt cat atc cct      576
Arg Arg Ser Val Glu Asp Ala Ile Glu Ser Arg Gly Val His Ile Pro
                180                 185                 190 tca gca ttg cgc cat cat aga cac aag cat gaa cat gaa gct gat gat      624
Ser Ala Leu Arg His His Arg His Lys His Glu His Glu Ala Asp Asp
            195                 200                 205 gat agg gac att gag ctt cca cat gtg gac cat ggc tat gta aag aat      672
Asp Arg Asp Ile Glu Leu Pro His Val Asp His Gly Tyr Val Lys Asn
        210                 215                 220
```

```
agg tca ttg cca ctt tct acc atc ata gac ata ctc aag cag aaa act        720
Arg Ser Leu Pro Leu Ser Thr Ile Ile Asp Ile Leu Lys Gln Lys Thr
225                 230                 235                 240 ggg aaa aat gat ata gat gtt ggg aaa ttg aga ctc tcg ctt tat gac        768
Gly Lys Asn Asp Ile Asp Val Gly Lys Leu Arg Leu Ser Leu Tyr Asp
            245                 250                 255 ata ttt ggg gaa gat gct agc cct aaa gtg aag aag ttc atg aag gtt        816
Ile Phe Gly Glu Asp Ala Ser Pro Lys Val Lys Lys Phe Met Lys Val
        260                 265                 270 atc ttg aat aaa ctc caa caa ggg gat ggt gga agt gga aaa caa ggt        864
Ile Leu Asn Lys Leu Gln Gln Gly Asp Gly Gly Ser Gly Lys Gln Gly
    275                 280                 285 gga atc ttg ggg cta gtg ggt agt ctt gcc caa gag ttt ctc aag caa        912
Gly Ile Leu Gly Leu Val Gly Ser Leu Ala Gln Glu Phe Leu Lys Gln
290                 295                 300 aag att gat tca agt gat gat ggt ggt tat gca aaa cct gcc atg gag        960
Lys Ile Asp Ser Ser Asp Asp Gly Gly Tyr Ala Lys Pro Ala Met Glu
305                 310                 315                 320 aca aag gtt gaa agc aaa tat gag gca tat gct gga aca agt tca gcc       1008
Thr Lys Val Glu Ser Lys Tyr Glu Ala Tyr Ala Gly Thr Ser Ser Ala
            325                 330                 335 aag ccg cgc ctt tca gac ggc gga att ctg atg agt ggt tgt caa aca       1056
Lys Pro Arg Leu Ser Asp Gly Gly Ile Leu Met Ser Gly Cys Gln Thr
        340                 345                 350 gac caa act tct gct gat gca agt cca gca ggt aac tct gcc agt gct       1104
Asp Gln Thr Ser Ala Asp Ala Ser Pro Ala Gly Asn Ser Ala Ser Ala
    355                 360                 365 tat gga gct ttt agc aat gca ata cag gct gtg att gag gag agt gat       1152
Tyr Gly Ala Phe Ser Asn Ala Ile Gln Ala Val Ile Glu Glu Ser Asp
370                 375                 380 ggt gct gtc aca aat caa gag att gtt ttg aag gca agg gag aag ctg       1200
Gly Ala Val Thr Asn Gln Glu Ile Val Leu Lys Ala Arg Glu Lys Leu
385                 390                 395                 400 aag agg gga ggt ttc aaa caa cgg cca gga ctt tac tgc agt gat gac       1248
Lys Arg Gly Gly Phe Lys Gln Arg Pro Gly Leu Tyr Cys Ser Asp Asp
            405                 410                 415 cat gtt gat ggt cct ttt gtg tgc tga                                   1275
His Val Asp Gly Pro Phe Val Cys
            420

<210> SEQ ID NO 2
<211> LENGTH: 424
<212> TYPE: PRT
<213> ORGANISM: Glycine max

<400> SEQUENCE: 2

Met Ala Lys Lys Ala Val Leu Ile Gly Ile Asn Tyr Pro Gly Thr Lys
1               5                   10                  15

Ala Glu Leu Lys Gly Cys Ile Asn Asp Val Trp Arg Met His Arg Cys
            20                  25                  30

Leu Ile Asp Arg Tyr Gly Phe Ser Glu Asp Ile Thr Val Leu Ile
        35                  40                  45

Asp Thr Asp Glu Ser Tyr Thr Glu Pro Thr Gly Lys Asn Ile Arg Ser
    50                  55                  60

Ala Leu Thr Arg Leu Ile Arg Ser Ala Arg Pro Gly Asp Val Leu Phe
65                  70                  75                  80

Val His Tyr Ser Gly His Gly Thr Arg Leu Pro Ala Glu Thr Gly Glu
                85                  90                  95

Asp Asp Asp Thr Gly Phe Asp Glu Cys Ile Val Pro Ser Asp Met Asn
```

```
                    100                 105                 110
Leu Ile Thr Asp Asp Phe Arg Glu Phe Val Asp Gly Val Pro Arg
            115                 120                 125
Glu Cys Lys Leu Thr Ile Val Ser Asp Ser Cys His Ser Gly Leu
        130                 135                 140
Ile Asp Gly Ala Lys Glu Gln Ile Gly Thr Ser Lys Gly Glu Gly
145                 150                 155                 160
Gln Gln His Ser Gly Ser Gly Gly Phe Gly Leu Ser Ser Phe Leu
                165                 170                 175
Arg Arg Ser Val Glu Asp Ala Ile Glu Ser Arg Gly Val His Ile Pro
            180                 185                 190
Ser Ala Leu Arg His His Arg His Lys His Glu His Glu Ala Asp Asp
            195                 200                 205
Asp Arg Asp Ile Glu Leu Pro His Val Asp His Gly Tyr Val Lys Asn
        210                 215                 220
Arg Ser Leu Pro Leu Ser Thr Ile Ile Asp Ile Leu Lys Gln Lys Thr
225                 230                 235                 240
Gly Lys Asn Asp Ile Asp Val Gly Lys Leu Arg Leu Ser Leu Tyr Asp
                245                 250                 255
Ile Phe Gly Glu Asp Ala Ser Pro Lys Val Lys Lys Phe Met Lys Val
            260                 265                 270
Ile Leu Asn Lys Leu Gln Gly Asp Gly Ser Gly Lys Gln Gly
        275                 280                 285
Gly Ile Leu Gly Leu Val Gly Ser Leu Ala Gln Glu Phe Leu Lys Gln
        290                 295                 300
Lys Ile Asp Ser Ser Asp Asp Gly Gly Tyr Ala Lys Pro Ala Met Glu
305                 310                 315                 320
Thr Lys Val Glu Ser Lys Tyr Glu Ala Tyr Ala Gly Thr Ser Ser Ala
                325                 330                 335
Lys Pro Arg Leu Ser Asp Gly Ile Leu Met Ser Gly Cys Gln Thr
            340                 345                 350
Asp Gln Thr Ser Ala Asp Ala Ser Pro Ala Gly Asn Ser Ala Ser Ala
        355                 360                 365
Tyr Gly Ala Phe Ser Asn Ala Ile Gln Ala Val Ile Glu Glu Ser Asp
        370                 375                 380
Gly Ala Val Thr Asn Gln Glu Ile Val Leu Lys Ala Arg Glu Lys Leu
385                 390                 395                 400
Lys Arg Gly Gly Phe Lys Gln Arg Pro Gly Leu Tyr Cys Ser Asp Asp
                405                 410                 415
His Val Asp Gly Pro Phe Val Cys
            420

<210> SEQ ID NO 3
<211> LENGTH: 465
<212> TYPE: DNA
<213> ORGANISM: Glycine max
<220> FEATURE:
<221> NAME/KEY: CDS
<222> LOCATION: (1)..(465)
<223> OTHER INFORMATION:

<400> SEQUENCE: 3 aag gtt atc ttg aat aaa ctc caa caa ggg gat ggt gga agt gga aaa     48
Lys Val Ile Leu Asn Lys Leu Gln Gln Gly Asp Gly Gly Ser Gly Lys
1               5                   10                  15 caa ggt gga atc ttg ggg cta gtg ggt agt ctt gcc caa gag ttt ctc     96
Gln Gly Gly Ile Leu Gly Leu Val Gly Ser Leu Ala Gln Glu Phe Leu
```

```
                    20                  25                  30
aag caa aag att gat tca agt gat gat ggt ggt tat gca aaa cct gcc     144
Lys Gln Lys Ile Asp Ser Ser Asp Asp Gly Gly Tyr Ala Lys Pro Ala
         35                  40                  45 atg gag aca aag gtt gaa agc aaa tat gag gca tat gct gga aca agt     192
Met Glu Thr Lys Val Glu Ser Lys Tyr Glu Ala Tyr Ala Gly Thr Ser
 50                  55                  60 tca gcc aag ccg cgc ctt tca gac ggc gga att ctg atg agt ggt tgt     240
Ser Ala Lys Pro Arg Leu Ser Asp Gly Gly Ile Leu Met Ser Gly Cys
 65                  70                  75                  80 caa aca gac caa act tct gct gat gca agt cca gca ggt aac tct gcc     288
Gln Thr Asp Gln Thr Ser Ala Asp Ala Ser Pro Ala Gly Asn Ser Ala
                 85                  90                  95 agt gct tat gga gct ttt agc aat gca ata cag gct gtg att gag gag     336
Ser Ala Tyr Gly Ala Phe Ser Asn Ala Ile Gln Ala Val Ile Glu Glu
            100                 105                 110 agt gat ggt gct gtc aca aat caa gag att gtt ttg aag gca agg gag     384
Ser Asp Gly Ala Val Thr Asn Gln Glu Ile Val Leu Lys Ala Arg Glu
        115                 120                 125 aag ctg aag agg gga ggt ttc aaa caa cgg cca gga ctt tac tgc agt     432
Lys Leu Lys Arg Gly Gly Phe Lys Gln Arg Pro Gly Leu Tyr Cys Ser
130                 135                 140 gat gac cat gtt gat ggt cct ttt gtg tgc tga                         465
Asp Asp His Val Asp Gly Pro Phe Val Cys
145                 150

<210> SEQ ID NO 4
<211> LENGTH: 154
<212> TYPE: PRT
<213> ORGANISM: Glycine max

<400> SEQUENCE: 4

Lys Val Ile Leu Asn Lys Leu Gln Gln Gly Asp Gly Gly Ser Gly Lys
1               5                   10                  15

Gln Gly Gly Ile Leu Gly Leu Val Gly Ser Leu Ala Gln Glu Phe Leu
            20                  25                  30

Lys Gln Lys Ile Asp Ser Ser Asp Asp Gly Gly Tyr Ala Lys Pro Ala
        35                  40                  45

Met Glu Thr Lys Val Glu Ser Lys Tyr Glu Ala Tyr Ala Gly Thr Ser
 50                  55                  60

Ser Ala Lys Pro Arg Leu Ser Asp Gly Gly Ile Leu Met Ser Gly Cys
 65                  70                  75                  80

Gln Thr Asp Gln Thr Ser Ala Asp Ala Ser Pro Ala Gly Asn Ser Ala
                 85                  90                  95

Ser Ala Tyr Gly Ala Phe Ser Asn Ala Ile Gln Ala Val Ile Glu Glu
            100                 105                 110

Ser Asp Gly Ala Val Thr Asn Gln Glu Ile Val Leu Lys Ala Arg Glu
        115                 120                 125

Lys Leu Lys Arg Gly Gly Phe Lys Gln Arg Pro Gly Leu Tyr Cys Ser
130                 135                 140

Asp Asp His Val Asp Gly Pro Phe Val Cys
145                 150

<210> SEQ ID NO 5
<211> LENGTH: 561
<212> TYPE: DNA
<213> ORGANISM: Glycine max
<220> FEATURE:
<221> NAME/KEY: CDS
<222> LOCATION: (1)..(543)
```

<223> OTHER INFORMATION:

<400> SEQUENCE: 5

```
atg gcg aaa aaa gcc gtt ttg atc gga ata aac tac ccg gga aca aag       48
Met Ala Lys Lys Ala Val Leu Ile Gly Ile Asn Tyr Pro Gly Thr Lys
1               5                   10                  15 gcg gag ctg aaa gga tgc ata aac gac gtg tgg agg atg cac cgc tgc       96
Ala Glu Leu Lys Gly Cys Ile Asn Asp Val Trp Arg Met His Arg Cys
                20                  25                  30 ctc atc gat cga tac ggt ttc tcc gaa gac gac atc acc gtt ttg atc      144
Leu Ile Asp Arg Tyr Gly Phe Ser Glu Asp Asp Ile Thr Val Leu Ile
            35                  40                  45 gac acg gac gaa tcc tac acg gag ccc acg ggg aaa aac att cgg tca      192
Asp Thr Asp Glu Ser Tyr Thr Glu Pro Thr Gly Lys Asn Ile Arg Ser
        50                  55                  60 gcg ctg acc aga ctc ata cga tcg gcg agg ccg ggg gac gtg ctg ttc      240
Ala Leu Thr Arg Leu Ile Arg Ser Ala Arg Pro Gly Asp Val Leu Phe
65                  70                  75                  80 gtg cat tac agc gga cat ggc acg cgc ctc ccc gcg gaa acc gga gag      288
Val His Tyr Ser Gly His Gly Thr Arg Leu Pro Ala Glu Thr Gly Glu
                85                  90                  95 gat gat gac act ggc ttt gat gaa tgc att gtt cct tct gat atg aac      336
Asp Asp Asp Thr Gly Phe Asp Glu Cys Ile Val Pro Ser Asp Met Asn
            100                 105                 110 ctc atc act gat gat gac ttc aga gaa ttt gta gat ggg gtc cct aga      384
Leu Ile Thr Asp Asp Asp Phe Arg Glu Phe Val Asp Gly Val Pro Arg
        115                 120                 125 gaa tgt aag ctc aca ata gta tca gat tct tgc cat agt ggt ggc cta      432
Glu Cys Lys Leu Thr Ile Val Ser Asp Ser Cys His Ser Gly Gly Leu
130                 135                 140 att gat gga gct aag gag cag ata gga act agc aca aag gga gaa ggg      480
Ile Asp Gly Ala Lys Glu Gln Ile Gly Thr Ser Thr Lys Gly Glu Gly
145                 150                 155                 160 caa caa cat tct ggt tct ggt tct ggc ttt gga tta tcc agt ttt ctt      528
Gln Gln His Ser Gly Ser Gly Ser Gly Phe Gly Leu Ser Ser Phe Leu
                165                 170                 175 cgt cgc tcc gtt gag gacgccatcg aatctcgt                              561
Arg Arg Ser Val Glu
            180
```

<210> SEQ ID NO 6
<211> LENGTH: 181
<212> TYPE: PRT
<213> ORGANISM: Glycine max

<400> SEQUENCE: 6

```
Met Ala Lys Lys Ala Val Leu Ile Gly Ile Asn Tyr Pro Gly Thr Lys
1               5                   10                  15

Ala Glu Leu Lys Gly Cys Ile Asn Asp Val Trp Arg Met His Arg Cys
                20                  25                  30

Leu Ile Asp Arg Tyr Gly Phe Ser Glu Asp Asp Ile Thr Val Leu Ile
            35                  40                  45

Asp Thr Asp Glu Ser Tyr Thr Glu Pro Thr Gly Lys Asn Ile Arg Ser
        50                  55                  60

Ala Leu Thr Arg Leu Ile Arg Ser Ala Arg Pro Gly Asp Val Leu Phe
65                  70                  75                  80

Val His Tyr Ser Gly His Gly Thr Arg Leu Pro Ala Glu Thr Gly Glu
                85                  90                  95

Asp Asp Asp Thr Gly Phe Asp Glu Cys Ile Val Pro Ser Asp Met Asn
            100                 105                 110
```

```
Leu Ile Thr Asp Asp Phe Arg Glu Phe Val Asp Gly Val Pro Arg
            115                 120                 125

Glu Cys Lys Leu Thr Ile Val Ser Asp Ser Cys His Ser Gly Gly Leu
130                 135                 140

Ile Asp Gly Ala Lys Glu Gln Ile Gly Thr Ser Thr Lys Gly Glu Gly
145                 150                 155                 160

Gln Gln His Ser Gly Ser Gly Ser Gly Phe Gly Leu Ser Ser Phe Leu
                165                 170                 175

Arg Arg Ser Val Glu
            180

<210> SEQ ID NO 7
<211> LENGTH: 134
<212> TYPE: PRT
<213> ORGANISM: Glycine max

<400> SEQUENCE: 7

Met Glu Gln Glu Asp Asn Thr Ile Ile Pro Thr Phe Leu Arg Lys Pro
1               5                   10                  15

Ala Glu Asp Gln Asn Asn Asn Ser Pro Thr Pro Ser His Ser Lys
            20                  25                  30

Ser Leu His Val Phe Arg Arg Ser Arg Arg Trp Arg Lys Glu Val
        35                  40                  45

Ala Val Lys Asp Ala Val Gln Glu Glu Asp Glu Glu Lys Glu Glu
    50                  55                  60

Gly Glu Asp Gly Gly Asp Asp Arg Glu Glu Ile Glu Arg Lys Ile His
65                  70                  75                  80

Ala Leu Gln Arg Ile Val Pro Gly Gly Glu Ser Leu Gly Val Asp Lys
                85                  90                  95

Leu Phe Asp Glu Thr Ala Gly Tyr Ile Leu Ala Leu Gln Tyr Gln Val
            100                 105                 110

Lys Ala Leu Arg Ala Leu Thr Gly Phe Phe Glu Lys Leu Glu Lys Glu
        115                 120                 125

Lys Thr Lys Phe Gly Gly
        130

<210> SEQ ID NO 8
<211> LENGTH: 128
<212> TYPE: PRT
<213> ORGANISM: Glycine max

<400> SEQUENCE: 8

Met Glu Gln Glu Asp Asn Thr Ile Ile Pro Thr Phe Leu Arg Lys Pro
1               5                   10                  15

Ala Ala Asp Gln Asn Asn Asn Asn Asn Asn Asn Ser Pro Thr Thr
            20                  25                  30

Pro Ser His Lys Ser Leu His Phe Arg Arg Ser Arg Arg Trp Arg
        35                  40                  45

Lys Glu Val Ala Val Lys Glu Asp Glu Val Asp Glu Gly Asp Asp
    50                  55                  60

Arg Glu Glu Ile Glu Arg Lys Ile His Ala Leu Gln Arg Ile Val Pro
65                  70                  75                  80

Gly Gly Glu Ser Leu Gly Val Asp Lys Leu Phe Asp Glu Thr Ala Gly
                85                  90                  95

Tyr Ile Leu Ala Leu Gln Tyr Gln Val Lys Ala Leu Arg Ala Leu Thr
            100                 105                 110
```

```
Gly Phe Phe Glu Lys Leu Glu Lys Glu Lys Thr Lys Phe Gly Gly Arg
            115                 120                 125

<210> SEQ ID NO 9
<211> LENGTH: 128
<212> TYPE: PRT
<213> ORGANISM: Glycine max

<400> SEQUENCE: 9

Met Glu Gln Glu Asp Asn Thr Ile Ile Pro Thr Phe Leu Arg Lys Pro
1               5                   10                  15

Ala Ala Asp Gln Asn Asn Asn Asn Asn Asn Asn Asn Ser Pro Thr
            20                  25                  30

Thr Pro Ser His Lys Ser Leu His Phe Arg Arg Ser Arg Arg Arg Trp
            35                  40                  45

Arg Lys Glu Val Ala Val Lys Glu Asp Glu Asp Val Asp Glu Gly Asp
    50                  55                  60

Asp Arg Glu Glu Ile Glu Arg Lys Ile Pro Ala Leu Gln Arg Ile Val
65                  70                  75                  80

Pro Gly Gly Glu Ser Leu Gly Val Asp Lys Leu Phe Asp Glu Thr Ala
                85                  90                  95

Gly Tyr Ile Leu Ala Leu Gln Tyr Gln Val Lys Ala Leu Arg Ala Leu
            100                 105                 110

Thr Gly Phe Phe Glu Lys Leu Glu Lys Glu Lys Thr Lys Phe Gly Gly
            115                 120                 125

<210> SEQ ID NO 10
<211> LENGTH: 32
<212> TYPE: DNA
<213> ORGANISM: Glycine max

<400> SEQUENCE: 10
cgcggatccg tatggcagca gcactggtcg gt                              32

<210> SEQ ID NO 11
<211> LENGTH: 31
<212> TYPE: DNA
<213> ORGANISM: Glycine max

<400> SEQUENCE: 11
gccgctcgag ctaaatccat ctattgccaa c                              31

<210> SEQ ID NO 12
<211> LENGTH: 32
<212> TYPE: DNA
<213> ORGANISM: Glycine max

<400> SEQUENCE: 12
cgcggatccg tatggcagca gcactggtcg gt                              32

<210> SEQ ID NO 13
<211> LENGTH: 31
<212> TYPE: DNA
<213> ORGANISM: Glycine max

<400> SEQUENCE: 13
gccgctcgag ccatgacaag ttctccactg c                              31

<210> SEQ ID NO 14
<211> LENGTH: 32
<212> TYPE: DNA
<213> ORGANISM: Glycine max
```

-continued

<400> SEQUENCE: 14
cgcggatccg taaagctcca tcaacatctc tg                32

<210> SEQ ID NO 15
<211> LENGTH: 29
<212> TYPE: DNA
<213> ORGANISM: Glycine max

<400> SEQUENCE: 15
gccgctcgag tgatgtggct agatcatgc                   29

<210> SEQ ID NO 16
<211> LENGTH: 31
<212> TYPE: DNA
<213> ORGANISM: Glycine max

<400> SEQUENCE: 16
cgcggatccg ttcgaagctt atgtacttga g                 31

<210> SEQ ID NO 17
<211> LENGTH: 31
<212> TYPE: DNA
<213> ORGANISM: Glycine max

<400> SEQUENCE: 17
gccgctcgag ctaaatccat ctattgccaa c                 31

<210> SEQ ID NO 18
<211> LENGTH: 32
<212> TYPE: DNA
<213> ORGANISM: Glycine max

<400> SEQUENCE: 18
cgcggatccg tatggcagca gcactggtcg gt                32

<210> SEQ ID NO 19
<211> LENGTH: 29
<212> TYPE: DNA
<213> ORGANISM: Glycine max

<400> SEQUENCE: 19
gccgctcgag tgatgtggct agatcatgc                   29

<210> SEQ ID NO 20
<211> LENGTH: 32
<212> TYPE: DNA
<213> ORGANISM: Glycine max

<400> SEQUENCE: 20
cgcggatccg taaagctcca tcaacatctc tg                32

<210> SEQ ID NO 21
<211> LENGTH: 31
<212> TYPE: DNA
<213> ORGANISM: Glycine max

<400> SEQUENCE: 21
gccgctcgag ctaaatccat ctattgccaa c                 31

<210> SEQ ID NO 22
<211> LENGTH: 41
<212> TYPE: DNA
<213> ORGANISM: Glycine max

<400> SEQUENCE: 22
cgaattctaa tacgactcac tatagggaac agccaccatg g                41

<210> SEQ ID NO 23
<211> LENGTH: 34
<212> TYPE: DNA
<213> ORGANISM: Glycine max

<400> SEQUENCE: 23
ggaacagcca ccatggcctc ctacccttat gatg                34

<210> SEQ ID NO 24
<211> LENGTH: 46
<212> TYPE: DNA
<213> ORGANISM: Glycine max

<400> SEQUENCE: 24
tttttttttt tttttttttt tttttttttt ggcaaggtag acaagc                46

<210> SEQ ID NO 25
<211> LENGTH: 41
<212> TYPE: DNA
<213> ORGANISM: Glycine max

<400> SEQUENCE: 25
cgaattctaa tacgactcac tatagggaac agccaccatg g                41

<210> SEQ ID NO 26
<211> LENGTH: 39
<212> TYPE: DNA
<213> ORGANISM: Glycine max

<400> SEQUENCE: 26
cttgtcatcg tcgtccttgt agtccatggt ggctgttcc                39

<210> SEQ ID NO 27
<211> LENGTH: 35
<212> TYPE: DNA
<213> ORGANISM: Glycine max

<400> SEQUENCE: 27
ggacgacgat gacaaggcag cagcactggt cggtg                35

<210> SEQ ID NO 28
<211> LENGTH: 38
<212> TYPE: DNA
<213> ORGANISM: Glycine max

<400> SEQUENCE: 28
gcctgcagtg agatccgcta ccatgacaag ttctccac                38

<210> SEQ ID NO 29
<211> LENGTH: 47
<212> TYPE: DNA
<213> ORGANISM: Glycine max

<400> SEQUENCE: 29
tttttttttt tttttttttt tttttttttt gcctgcagtg agatccg                47

<210> SEQ ID NO 30
<211> LENGTH: 41
<212> TYPE: DNA
<213> ORGANISM: Glycine max

```
<400> SEQUENCE: 30
cgaattctaa tacgactcac tagggaac agccaccatg g                  41

<210> SEQ ID NO 31
<211> LENGTH: 39
<212> TYPE: DNA
<213> ORGANISM: Glycine max

<400> SEQUENCE: 31
cttgtcatcg tcgtccttgt agtccatggt ggctgttcc                   39

<210> SEQ ID NO 32
<211> LENGTH: 35
<212> TYPE: DNA
<213> ORGANISM: Glycine max

<400> SEQUENCE: 32
ggacgacgat gacaagaaag ctccatcaac atctc                       35

<210> SEQ ID NO 33
<211> LENGTH: 38
<212> TYPE: DNA
<213> ORGANISM: Glycine max

<400> SEQUENCE: 33
gcctgcagtg agatccgcta tgatgtggct agatcatg                    38

<210> SEQ ID NO 34
<211> LENGTH: 47
<212> TYPE: DNA
<213> ORGANISM: Glycine max

<400> SEQUENCE: 34
tttttttttt tttttttttt tttttttttt gcctgcagtg agatccg          47

<210> SEQ ID NO 35
<211> LENGTH: 41
<212> TYPE: DNA
<213> ORGANISM: Glycine max

<400> SEQUENCE: 35
cgaattctaa tacgactcac tagggaac agccaccatg g                  41

<210> SEQ ID NO 36
<211> LENGTH: 39
<212> TYPE: DNA
<213> ORGANISM: Glycine max

<400> SEQUENCE: 36
cttgtcatcg tcgtccttgt agtccatggt ggctgttcc                   39

<210> SEQ ID NO 37
<211> LENGTH: 35
<212> TYPE: DNA
<213> ORGANISM: Glycine max

<400> SEQUENCE: 37
ggacgacgat gacaaggcag cagcactggt cggtg                       35

<210> SEQ ID NO 38
<211> LENGTH: 38
<212> TYPE: DNA
```

```
<210> SEQ ID NO 38

<400> SEQUENCE: 38
gcctgcagtg agatccgcta tgatgtggct agatcatg                              38

<210> SEQ ID NO 39
<211> LENGTH: 47
<212> TYPE: DNA
<213> ORGANISM: Glycine max

<400> SEQUENCE: 39
tttttttttt tttttttttt tttttttttt gcctgcagtg agatccg                    47

<210> SEQ ID NO 40
<211> LENGTH: 34
<212> TYPE: DNA
<213> ORGANISM: Glycine max

<400> SEQUENCE: 40
gctctagact cgagaggtga tagcagcaac aaac                                  34

<210> SEQ ID NO 41
<211> LENGTH: 34
<212> TYPE: DNA
<213> ORGANISM: Glycine max

<400> SEQUENCE: 41
ccatcgatgg taccacgatg attccagtat gctg                                  34

<210> SEQ ID NO 42
<211> LENGTH: 35
<212> TYPE: DNA
<213> ORGANISM: Glycine max

<400> SEQUENCE: 42
gctctagaga attcccaagc ttcctgattc tgttg                                 35

<210> SEQ ID NO 43
<211> LENGTH: 35
<212> TYPE: DNA
<213> ORGANISM: Glycine max

<400> SEQUENCE: 43
ccatcgatgg tacccatgtc atgaggcatc tttgc                                 35

<210> SEQ ID NO 44
<211> LENGTH: 35
<212> TYPE: DNA
<213> ORGANISM: Glycine max

<400> SEQUENCE: 44
gctctagact cgagcaactg cagaagaatt cctgc                                 35

<210> SEQ ID NO 45
<211> LENGTH: 36
<212> TYPE: DNA
<213> ORGANISM: Glycine max

<400> SEQUENCE: 45
ccatcgatgg tacccatat gctacatgtg attcac                                 36

<210> SEQ ID NO 46
<211> LENGTH: 35
<212> TYPE: DNA
```

```
<400> SEQUENCE: 46
gctctagact cgagctatga ccttcaatcg atgtg                                35

<210> SEQ ID NO 47
<211> LENGTH: 35
<212> TYPE: DNA
<213> ORGANISM: Glycine max

<400> SEQUENCE: 47
cccaagcttg gtaccatcag tgcttgcaaa ggcag                                35

<210> SEQ ID NO 48
<211> LENGTH: 34
<212> TYPE: DNA
<213> ORGANISM: Glycine max

<400> SEQUENCE: 48
gctctagact cgaggagctt ccttcactta aatc                                 34

<210> SEQ ID NO 49
<211> LENGTH: 34
<212> TYPE: DNA
<213> ORGANISM: Glycine max

<400> SEQUENCE: 49
ccatcgatgg taccctcaac atgttgtaag cagg                                 34

<210> SEQ ID NO 50
<211> LENGTH: 34
<212> TYPE: DNA
<213> ORGANISM: Glycine max

<400> SEQUENCE: 50
gctctagact cgagatcata cccacattcc tcag                                 34

<210> SEQ ID NO 51
<211> LENGTH: 35
<212> TYPE: DNA
<213> ORGANISM: Glycine max

<400> SEQUENCE: 51
ccatcgatgg tacccatcaa cctccaaact ttgtc                                35

<210> SEQ ID NO 52
<211> LENGTH: 35
<212> TYPE: DNA
<213> ORGANISM: Glycine max

<400> SEQUENCE: 52
gctctagact cgagcagcta tggattctga agttc                                35

<210> SEQ ID NO 53
<211> LENGTH: 34
<212> TYPE: DNA
<213> ORGANISM: Glycine max

<400> SEQUENCE: 53
ccatcgatgg tacccatgca agctctgacc aatc                                 34

<210> SEQ ID NO 54
<211> LENGTH: 35
<212> TYPE: DNA
<213> ORGANISM: Glycine max
```

```
<400> SEQUENCE: 54
gctctagact cgagaccgaa gcataagtta gttcc                              35

<210> SEQ ID NO 55
<211> LENGTH: 35
<212> TYPE: DNA
<213> ORGANISM: Glycine max

<400> SEQUENCE: 55
ccatcgatgg tacccatctt ttgaatccag agagc                              35

<210> SEQ ID NO 56
<211> LENGTH: 36
<212> TYPE: DNA
<213> ORGANISM: Glycine max

<400> SEQUENCE: 56
gctctagact cgagcacatt gagagtggag atatac                             36

<210> SEQ ID NO 57
<211> LENGTH: 37
<212> TYPE: DNA
<213> ORGANISM: Glycine max

<400> SEQUENCE: 57
cccaagcttg gtacccaatg tatcagtgct tgcaaag                            37

<210> SEQ ID NO 58
<211> LENGTH: 35
<212> TYPE: DNA
<213> ORGANISM: Glycine max

<400> SEQUENCE: 58
gctctagact cgaggatgga aatactggca gtatc                              35

<210> SEQ ID NO 59
<211> LENGTH: 35
<212> TYPE: DNA
<213> ORGANISM: Glycine max

<400> SEQUENCE: 59
ccatcgatgg tacccatacg ccagttaatt aagtc                              35

<210> SEQ ID NO 60
<211> LENGTH: 34
<212> TYPE: DNA
<213> ORGANISM: Glycine max

<400> SEQUENCE: 60
gctctagact cgaggcagta gagcagttcc taac                               34

<210> SEQ ID NO 61
<211> LENGTH: 34
<212> TYPE: DNA
<213> ORGANISM: Glycine max

<400> SEQUENCE: 61
ccatcgatgg taccgacaag ctagtgtcac catc                               34

<210> SEQ ID NO 62
<211> LENGTH: 34
<212> TYPE: DNA
<213> ORGANISM: Glycine max
```

```
-continued

<400> SEQUENCE: 62
gctctagact cgagtggagc taaggagcag atag                                   34

<210> SEQ ID NO 63
<211> LENGTH: 35
<212> TYPE: DNA
<213> ORGANISM: Glycine max

<400> SEQUENCE: 63
ccatcgatgg taccaccacc atcatcactt gaatc                                  35
```

METACASPASE II IN ENGINEERING SOYBEAN FOR DISEASE RESISTANCE

CROSS-REFERENCE TO RELATED APPLICATIONS

This application claims priority under 35 U.S.C. §119(e) to provisional application Ser. No. 60/911,342 filed Apr. 12, 2007, herein incorporated by reference in its entirety.

FIELD OF THE INVENTION

The present invention is in the field of soybean genetics. More specifically, the invention relates to nucleic acid molecules from regions of the soybean genome, which are associated with soybean pathogen resistance, particularly to *Phytophthora*. The invention also relates to proteins encoded by such nucleic acid molecules as well as antibodies capable of recognizing these proteins. The invention also relates to nucleic acid markers from regions of the soybean genome, which are associated with *Phytophthora* resistance. Moreover, the invention relates to uses of such molecules, including, transforming *Phytophthora* sensitive soybean with constructs containing nucleic acid molecules from regions in the soybean genome, which are associated with *Phytophthora* resistance. Furthermore, the invention relates to the use of such molecules in a plant breeding program.

BACKGROUND OF THE INVENTION

Soybean [*Glycine max* L. (Merrill)] is a major oil seed crop and is grown throughout much of the world. The United States alone produces over half of the world output. Soybean seed typically contains 40% protein and 20% oil and is used primarily for livestock feed and industrial purposes, in addition to human consumption. In North America, soybean suffers yield loss from the root and stem rot disease caused by oomycete pathogen *Phytophthora sojae*. In the United States the annual crop losses from this disease were valued to about 0.2-0.3 billion dollars (Wrather et al. 2001). Plant resistance to this and other sort of pathogens present a major problem to soybean growers.

Plants do not have circulatory or any auto-immune systems that are integral parts of mammalian defenses to pathogens and instead have evolved unique defense mechanisms to defeat invading pathogenic organisms. Plants rely primarily on active defense mechanisms to combat and resist damage from invading pathogens. These defense mechanisms are regulated by single race-specific disease resistance (R) genes that encode receptors to recognize specific pathogen derived ligand molecules (Dangl and Jones 2001). The genetic basis of this recognition phenomenon was described by Flor as a 'gene for gene' relationship in the flax and *Melampsora lini* interaction (Flor 1955). In recent years over 30 R genes have been isolated (Dangl and Jones 2001; Hulbert et al. 2001). Cloning of resistance genes and their corresponding avirulence genes has facilitated the demonstration of the in vivo interactions between products of resistance and avirulence genes as a proof for the Flor's hypothesis (Leister et al. 1996; Scofield et al. 1996; Tang et al. 1996 2000).

Several plant disease resistance genes that follow the classical gene-for-gene hypothesis (Flor, 1955) have been cloned. These genes can be classified into four major groups based on the structures of their protein products: i) proteins with serine/threonine kinase activity, e.g., Pto (Martin et al., 1993); ii) proteins with nucleotide binding sites (NBS) and leucine rich repeat regions (LRR), e.g. RPS2, N, L6, RPM1, Prf, M, I2 and RPP5 (Anderson et al., 1997; Bent et al. 1994; Grant et al., 1995; Lawrence et al., 1995; Mindrinos et al., 1994; Ori et al., 1997; Parker et al., 1997; Salmeron et al., 1996; Whitham et al., 1994); iii) proteins with leucine rich repeat regions and transmembrane domain, e.g. Cf2, Cf4, Cf5, Cf9, and Hs1$^{pro-1}$ (Cai et al., 1997; Dixon et al., 1996; Jones et al., 1994; Thomas et al., 1997) and iv) proteins with leucine rich repeat regions, transmembrane and serine/threonine kinase domains, e.g. Xa21 (Song et al., 1995). The group carrying genes with NBS and LRR motifs can be sub-divided into two sub-groups. They are: iia) TIR NBS-LRR genes that carry an N-terminal TIR domain with homologies to Toll receptor of *Drosophila* and interleukin-1R receptor of mammals, and iib) non-TIR NBS-LRR genes that carry no TIR domain (Meyers et al., 1999). Most of the disease resistance genes cloned recently belongs to non-TIR group, which includes genes that confer resistance to viruses, bacteria, fungi, oomycetes, nematodes and aphids. TIR NBS-LRR type genes are most likely absent in the Poaceae (Meyers et al., 1999; Pan et al., 2000). Meyers and co-workers (1999) concluded that *Arabidopsis* genome contains approximately 200 genes that encode NBS sequences and are located in 21 genomic clusters and 14 isolated loci. Structural conservation among resistance genes from a wide range of plant species prompted several groups to identify putative resistance genes from *Arabidopsis*, potato, rice, soybean and wheat (Botella et al., 1997; Kanazin et al., 1996; Leister et al., 1998; Leister et al., 1996a; Yu et al., 1996).

Rps (Resistance *Phytophthora sojae*) loci have provided a reasonable protection to soybean crops against *Phytophthora sojae* over the last three decades. There are several physiological races of this fungal pathogen. The number of races is increasing rapidly. For example, in 1994 there were 37 recorded races of the fungus (Förster et al., 1994). Now the number is 45 (Abney et al., 1997). Schmitthenner and his co-workers (1994) concluded that *P. sojae* is a highly variable pathogen and exists in soil as a wide variety of virulence phenotypes to which most Rps genes are ineffective. They also concluded that, unless new Rps genes are identified or existing Rps genes are pyramided in single cultivars, resistance available in the present day cultivars might not be effective in controlling the disease in future.

At present, there are 14 Rps genes that confer race-specific resistance of soybean to different physiological races of *P. sojae*. These genes were obtained from different *Glycine max* lines, and mapped to eight loci (Anderson and Buzzell, 1992; Polzin et al., 1994; Schmitthenner, 1989; Burnham et al. 2003). Of these 14 genes, five are mapped to Rps1 and three to Rps3. The genetics of resistance conferred by Rps genes is well established. Recently, genetics of most of the avirulence genes (Avr) that correspond to specific Rps genes have also been reported (Gijzen et al. 1996; Tyler et al., 1995; Whisson et al., 1994; 1995). The interactions between these 14 Rps genes with the corresponding genes for avirulence in *P. sojae* follow the 'gene-for-gene' hypothesis (Flor, 1955).

Thus there is a continuing need for developing and understanding molecules associated with *Phytophthora* resistance in plants.

SUMMARY OF THE INVENTION

In one aspect, this invention relates to a metacaspase II DNA sequence (RIP 13) isolated from soybean (*Glycine max*) which is associated with *Phytophthora* resistance. Also according to the invention, protein sequences are disclosed which are encoded by this sequence. This sequence alone, or in combination with other sequences, can be used to improve the soybean resistance to fungal pathogens such as *Phytophthora*. In another aspect of the present invention, expression cassettes and transformation vectors comprising the isolated nucleotide sequences are disclosed. The transformation vectors can be used to transform plants and express these pathogen control genes in the transformed cells. Transformed cells as well as regenerated transgenic plants and seeds containing and expressing the isolated DNA sequences and protein products are also provided.

The present invention includes and provides a method of investigating an haplotype of a soybean plant comprising: (A) isolating nucleic acid molecules from the soybean plant; (B) determining the nucleic acid sequence of a metacaspase allele or part thereof; and, (C) comparing the nucleic acid sequence of the allele or part thereof to a reference nucleic acid sequence. The present invention includes and provides a method of introgressing *Phytophthora* resistance or partial *Phytophthora* resistance into a soybean plant comprising: performing marker assisted selection of the soybean plant with a nucleic acid marker, wherein the nucleic acid marker specifically hybridizes with a nucleic acid molecule encoding metacaspase II encoding sequences and alleles of the invention and, selecting the soybean plant based on the marker assisted selection.

The present invention includes and provides a method of investigating a metacaspase haplotype of a soybean plant comprising: (A) isolating nucleic acid molecules from the soybean plant; (B) determining the nucleic acid sequence of an metacaspase allele or part thereof; and (C) comparing the nucleic acid sequence of the metacaspase allele or part thereof to a reference nucleic acid sequence.

Therefore, in one aspect, the present invention relates to an isolated nucleic acid comprising an isolated polynucleotide sequence encoding a metacaspase gene product that interacts with Rps1-k-2 for *Phytophthora* resistance. In a further aspect, the present invention includes a nucleic acid selected from: (a) an isolated polynucleotide encoding a polypeptide of the present invention; (b) a polynucleotide having at least 90% or 95% identity to a polynucleotide of the present invention; (c) a polynucleotide comprising at least 50 or more nucleotides in length which hybridizes under high stringency conditions to a polynucleotide of the present invention; (d) a polynucleotide comprising a polynucleotide of the present invention; and (e) a polynucleotide which is complementary to the polynucleotide of (a) to (e).

In another aspect, the present invention relates to a recombinant expression cassette comprising a nucleic acid as described, supra. Additionally, the present invention relates to a vector containing the recombinant expression cassette. Further, the vector containing the recombinant expression cassette can facilitate the transcription and translation of the nucleic acid in a host cell. The present invention also relates to host cells able to express the polynucleotide of the present invention. A number of host cells could be used, such as but not limited to, microbial, mammalian, plant, or insect. Thus the invention is also directed to transgenic cells, containing the nucleic acids of the present invention as well as cells, plants, tissue cultures and ultimately lines derived therefrom. The invention also relates to vectors and cassettes designed to down regulate, or inhibit the expression of the metacaspase II protein of the invention for modulation of the Rspk-1-2 interaction, or for delination of information about the regulatory pathways involving the same.

This invention also provides an isolated polypeptide comprising (a) a polypeptide comprising at least 90% or 95% sequence identity to a polypeptide of the present invention (b) a polypeptide encoded by a nucleic acid of the present invention; and (c) a polypeptide comprising Rps1-k-2 modulating activity and comprising the conserved structural domain motifs of the invention.

Another embodiment of the subject invention comprises a methods for engineering broad spectrum pathogen resistance in soybean plants by modulating the expression of metacaspase II proteins. Plants tolerance to *Phytophthora* and other soybean pathogens may be improved by elucidating the pathways that regulate gene transcription involved in enhancing accumulation of products shown to be associated with expression of pathogen resistance, methods for providing for increased non specific resistance to particularly virulent races or strains of pathogenic agents including *P. sojae*, *Pseudomonas syringae* pv. *glycenia* (Psg), soybean cyst nematode (SCN), or soybean mosaic virus.

Nucleotide sequences isolated from the metacaspase II locus including the metacaspase gene family can be used in developing perfect molecular markers that can be routinely used in breeding programs for incorporating *Phytophthora* resistance into new soybean cultivars.

The metacaspase gene family will pave the way for better understanding the mechanism of *Phytophthora* resistance and also for isolating other important proteins involved in the expression of resistance, and thereby, this invention will lead to the development of a strong background for genetic engineering of soybean for disease resistance.

Units, prefixes, and symbols may be denoted in their SI accepted form. Unless otherwise indicated, nucleic acids are written left to right in 5' to 3' orientation; amino acid sequences are written left to right in amino to carboxy orientation, respectively. Numeric ranges are inclusive of the numbers defining the range and include each integer within the defined range. Amino acids may be referred to herein by either their commonly known three letter symbols or by the one-letter symbols recommended by the IUPAC-IUB Biochemical nomenclature Commission. Nucleotides, likewise, may be referred to by their commonly accepted single-letter codes. Unless otherwise provided for, software, electrical, and electronics terms as used herein are as defined in The New IEEE Standard Dictionary of Electrical and Electronics Terms (5$^{th}$ edition, 1993). The terms defined below are more fully defined by reference to the specification as a whole.

By "amplified" is meant the construction of multiple copies of a nucleic acid sequence or multiple copies complementary to the nucleic acid sequence using at least one of the nucleic acid sequences as a template. Amplification systems include the polymerase chain reaction (PCR) system, ligase chain reaction (LCR) system, nucleic acid sequence based amplification (NASBA, Canteen, Mississauga, Ontario), Q-Beta Replicase systems, transcription-based amplification system (TAS), and strand displacement amplification (SDA). See, e.g., *Diagnostic Molecular Microbiology: Principles and Applications*, D. H. Persing et al., Ed., American Society for Microbiology, Washington, D.C. (1993). The product of amplification is termed an amplicon.

As used herein, "chromosomal region" includes reference to a length of a chromosome that may be measured by reference to the linear segment of DNA that it comprises. The chromosomal region can be defined by reference to two unique DNA sequences, i.e., markers.

The term "conservatively modified variants" applies to both amino acid and nucleic acid sequences. With respect to particular nucleic acid sequences, conservatively modified variants refers to those nucleic acids which encode identical or conservatively modified variants of the amino acid sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also, by reference to the genetic code, describes every possible silent variation of the nucleic acid. One of ordinary skill will recognize that each codon in a nucleic acid (except AUG, which is ordinarily the only codon for methionine; and UGG, which is ordinarily the only codon for tryptophan) can be modified to yield a functionally identical molecule. Accordingly, each silent variation of a nucleic acid which encodes a polypeptide of the present invention is implicit in each described polypeptide sequence and is within the scope of the present invention.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7, or 10 alterations can be made. Conservatively modified variants typically provide similar biological activity as the unmodified polypeptide sequence from which they are derived. For example, substrate specificity, enzyme activity, or ligand/receptor binding is generally at least 30%, 40%, 50%, 60%, 70%, 80%, or 90% of the native protein for its native substrate. Conservative substitution tables providing functionally similar amino acids are well known in the art.

The following six groups each contain amino acids that are conservative substitutions for one another:
  1) Alanine (A), Serine (S), Threonine (T);
  2) Aspartic acid (D), Glutamic acid (E);
  3) Asparagine (N), Glutamine (Q);
  4) Arginine (R), Lysine (K);
  5) Isoleucine (I), Leucine (L), Methionine (M), Valine (V); and
  6) Phenylalanine (F), Tyrosine (Y), Tryptophan (W).
See also, Creighton (1984) *Proteins W.H. Freeman and Company*.

By "encoding" or "encoded", with respect to a specified nucleic acid, is meant comprising the information for translation into the specified protein. A nucleic acid encoding a protein may comprise non-translated sequences (e.g., introns) within translated regions of the nucleic acid, or may lack such intervening non-translated sequences (e.g., as in cDNA). The information by which a protein is encoded is specified by the use of codons. Typically, the amino acid sequence is encoded by the nucleic acid using the "universal" genetic code. However, variants of the universal code, such as are present in some plant, animal, and fungal mitochondria, the bacterium *Mycoplasma capricolum*, or the ciliate Macronucleus, may be used when the nucleic acid is expressed therein.

When the nucleic acid is prepared or altered synthetically, advantage can be taken of known codon preferences of the intended host where the nucleic acid is to be expressed. For example, although nucleic acid sequences of the present invention may be expressed in both monocotyledonous and dicotyledonous plant species, sequences can be modified to account for the specific codon preferences and GC content preferences of monocotyledons or dicotyledons as these preferences have been shown to differ (Murray et al. *Nucl. Acids Res.* 17:477-498 (1989)).

As used herein "full-length sequence" in reference to a specified polynucleotide or its encoded protein means having the entire amino acid sequence of, a native (non-synthetic), endogenous, biologically active form of the specified protein. Methods to determine whether a sequence is full-length are well known in the art including such exemplary techniques as northern or western blots, primer extensions, SI protection, and ribonuclease protection. See, e.g., *Plant Molecular Biology: A Laboratory Manual*, Clark, Ed., Springer-Verlag, Berlin (1997). Comparison to known full-length homologous (orthologous and/or paralogous) sequences can also be used to identify full-length sequences of the present invention. Additionally, consensus sequences typically present at the 5' and 3' untranslated regions of mRNA aid in the identification of a polynucleotide as full-length. For example, the consensus sequence ANNNNAUGG, where the underlined codon represents the N-terminal methionine, aids in determining whether the polynucleotide has a complete 5' end. Consensus sequences at the 3' end, such as polyadenylation sequences, aid in determining whether the polynucleotide has a complete 3' end.

As used herein, "heterologous" in reference to a nucleic acid is a nucleic acid that originates from a foreign species, or, if from the same species, is substantially modified from its native form in composition and/or genomic locus by deliberate human intervention. For example, a promoter operably linked to a heterologous structural gene is from a species different from that from which the structural gene was derived, or, if from the same species, one or both are substantially modified from their original form. A heterologous protein may originate from a foreign species or, if from the same species, is substantially modified from its original form by deliberate human intervention.

By "host cell" is meant a cell which contains a vector and supports the replication and/or expression of the vector. Host cells may be prokaryotic cells such as *E. coli*, or eukaryotic cells such as yeast, insect, amphibian, or mammalian cells. Preferably, host cells are monocotyledonous or dicotyledonous plant cells. A particularly preferred monocotyledonous host cell is a maize host cell.

The term "hybridization complex" includes reference to a duplex nucleic acid structure formed by two single-stranded nucleic acid sequences selectively hybridized with each other.

The term "introduced" in the context of inserting a nucleic acid into a cell, means "transfection" or "transformation" or "transduction" and includes reference to the incorporation of a nucleic acid into a eukaryotic or prokaryotic cell where the nucleic acid may be incorporated into the genome of the cell (e.g., chromosome, plasmid, plastid or mitochondrial DNA), converted into an autonomous replicon, or transiently expressed (e.g., transfected mRNA).

The term "isolated" refers to material, such as a nucleic acid or a protein, which is: (1) substantially or essentially free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material can be performed on the material within or removed from its natural state. For example, a naturally occurring nucleic acid becomes an isolated nucleic acid if it is altered, or if it is transcribed from DNA which has been altered, by means of human intervention performed within the cell from which it originates. See, e.g., Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (e.g., a promoter) becomes isolated if it is introduced by non-naturally occurring means to a locus of the genome not native to that nucleic acid. Nucleic acids which are "isolated" as defined herein, are also referred to as "heterologous" nucleic acids.

As used herein, "localized within the chromosomal region defined by and including" with respect to particular markers includes reference to a contiguous length of a chromosome delimited by and including the stated markers.

As used herein, "marker" includes reference to a locus on a chromosome that serves to identify a unique position on the chromosome. A "polymorphic marker" includes reference to a marker which appears in multiple forms (alleles) such that different forms of the marker, when they are present in a homologous pair, allow transmission of each of the chromosomes of that pair to be followed. A genotype may be defined by use of one or a plurality of markers.

As used herein, the term "metacaspase" or "metacaspase II" shall include any amino acid sequences which retain one or more of the properties of metacaspase enzymes in general. They also must be capable of interacting with the N-terminal region of an Rps1-k-2 protein as described herein. Such proteins may include the 424 amino acid sequence showing in FIG. 5 and any conservatively modified variants, fragments, and homologs or full length sequences incorporating the same which retain the Rps1-k-2 interacting activity described herein.

As used herein, "nucleic acid" includes reference to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

By "nucleic acid library" is meant a collection of isolated DNA or cDNA molecules which comprise and substantially represent the entire transcribed fraction of a genome of a specified organism. Construction of exemplary nucleic acid libraries, such as genomic and cDNA libraries, is taught in standard molecular biology references such as Berger and Kimmel, *Guide to Molecular Cloning Techniques, Methods in Enzymology*, Vol. 152, Academic Press, Inc., San Diego, Calif. (Berger); Sambrook et al., *Molecular Cloning—A Laboratory Manual*, 2$^{nd}$ ed., Vol. 1-3 (1989); and *Current Protocols in Molecular Biology*, F. M. Ausubel et al., Eds., Current Protocols, a joint venture between Greene Publishing Associates, Inc. and John Wiley & Sons, Inc. (1994).

As used herein "operably linked" includes reference to a functional linkage between a promoter and a second sequence, wherein the promoter sequence initiates and mediates transcription of the DNA sequence corresponding to the second sequence. Generally, operably linked means that the nucleic acid sequences being linked are contiguous and, where necessary to join two protein coding regions, contiguous and in the same reading frame.

As used herein, the term "plant" can include reference to whole plants, plant parts or organs (e.g., leaves, stems, roots, etc.), plant cells, seeds and progeny of same. Plant cell, as used herein, further includes, without limitation, cells obtained from or found in: seeds, suspension cultures, embryos, meristematic regions, callus tissue, leaves, roots, shoots, gametophytes, sporophytes, pollen, and microspores. Plant cells can also be understood to include modified cells, such as protoplasts, obtained from the aforementioned tissues. The class of plants which can be used in the methods of the invention is generally as broad as the class of higher plants amenable to transformation techniques, including both monocotyledonous and dicotyledonous plants. Particularly preferred plants include maize, soybean, sunflower, sorghum, canola, wheat, alfalfa, cotton, rice, barley, and millet.

As used herein, "polynucleotide" includes reference to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide can be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons as "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein, that protein is specifically reactive to antibodies elicited to the same protein but consisting entirely of naturally occurring amino acids. The terms "polypeptide", "peptide" and "protein" are also inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides are not entirely linear. For instance, polypeptides may be branched as a result of ubiquitination, and they may be circular, with or without branching, generally as a result of posttranslation events, including natural processing event and events brought about by human manipulation which do not occur naturally. Circular, branched and branched circular polypeptides may be synthesized by non-translation natural process and by entirely synthetic methods, as well. Further, this invention contemplates the use of both the methionine-containing and the methionine-less amino terminal variants of the protein of the invention.

As used herein "promoter" includes reference to a region of DNA upstream from the start of transcription and involved in recognition and binding of RNA polymerase and other proteins to initiate transcription. A "plant promoter" is a promoter capable of initiating transcription in plant cells whether or not its origin is a plant cell. Exemplary plant promoters include, but are not limited to, those that are obtained from plants, plant viruses, and bacteria which comprise genes expressed in plant cells such as *Agrobacterium* or *Rhizobium*. Examples of promoters under developmental control include promoters that preferentially initiate transcription in certain tissues, such as leaves, roots, or seeds. Such promoters are referred to as "tissue preferred". Promoters which initiate transcription only in certain tissue are referred to as "tissue specific". A "cell type" specific promoter primarily drives expression in certain cell types in one or more organs, for example, vascular cells in roots or leaves. An "inducible" or "repressible" promoter is a promoter which is under environmental control. Examples of environmental conditions that may effect transcription by inducible promoters include anaerobic conditions or the presence of light. Tissue specific, tissue preferred, cell type specific, and inducible promoters constitute the class of "non-constitutive" promoters. A "constitutive" promoter is a promoter which is active under most environmental conditions.

As used herein "recombinant" includes reference to a cell or vector, that has been modified by the introduction of a heterologous nucleic acid or that the cell is derived from a cell so modified. Thus, for example, recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation/transduction/transposition) such as those occurring without deliberate human intervention.

As used herein, a "recombinant expression cassette" is a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "residue" or "amino acid residue" or "amino acid" are used interchangeably herein to refer to an amino acid that is incorporated into a protein, polypeptide, or peptide (collectively "protein"). The amino acid may be a naturally occurring amino acid and, unless otherwise limited, may encompass non-natural analogs of natural amino acids that can function in a similar manner as naturally occurring amino acids.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 80% sequence identity, preferably 90% sequence identity, and most preferably 100% sequence identity (i.e., complementary) with each other.

The term "stringent conditions" or "stringent hybridization conditions" includes reference to conditions under which a probe will hybridize to its target sequence, to a detectably greater degree than to other sequences (e.g., at least 2-fold over background). Stringent conditions are sequence-dependent and be different in different circumstances. By controlling the stringency of the hybridization and/or washing conditions, target sequences can be identified which are 100% complementary to the probe (homologous probing). Alternatively, stringency conditions can be adjusted to allow some mismatching in sequences so that lower degrees of similarity are detected (heterologous probing). Generally, a probe is less than about 1000 nucleotides in length, optionally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1 M NaCl, 1% SDS at 37° C., and a wash in 0.5× to 1×SSC at 55 to 50° C. Exemplary high stringency conditions include hybridization in 50% formamide, 1 M NaCl, 1% SDS at 37° C., and a wash in 0.1×SSC at 60 to 65° C. for 20 minutes.

Specificity is typically the function of post-hybridization washes, the critical factors being the ionic strength and temperature of the final wash solution. For DNA-DNA hybrids, the $T_m$ can be approximated from the equation of Meinkoth and Wahl, *Anal. Biochem.*, 138:267-284 (1984): $T_m=81.5°$ C.$+16.6$ (log M)$+0.41$ (% GC)$-0.61$ (% form)$-500/L$; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of the complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3, or 4° C. lower than the thermal melting point ($T_m$); moderately stringent conditions can utilize a hybridization and/or wash at 6, 7, 8, 9, or 10° C. lower than the thermal melting point ($T_m$); low stringency conditions can utilize a hybridization and/or wash at 11, 12, 13, 14, 15, or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution) it is preferred to increase the SSC concentration so that a higher temperature can be used. An extensive guide to the hybridization of nucleic acids is found in Tijssen, *Laboratory Techniques in Biochemistry and Molecular Biology—Hybridization with Nucleic Acids Probes*, Part I, Chapter 2, Ausubel, et al., Eds., Greene Publishing and Wiley-Interscience, New York (1995). In general a high stringency wash is 2×15 min in 0.5×SSC containing 0.1% SDS at 65° C.

As used herein, "transgenic plant" includes reference to a plant which comprises within its genome a heterologous polynucleotide. Generally, the heterologous polynucleotide is stably integrated within the genome such that the polynucleotide is passed on to successive generations. The heterologous polynucleotide may be integrated into the genome alone or as part of a recombinant expression cassette. "Transgenic" is used herein to include any cell, cell line, callus, tissue, plant part or plant, the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

As used herein, "vector" includes reference to a nucleic acid used in transfection of a host cell and into which can be inserted a polynucleotide. Vectors are often replicons. Expression vectors permit transcription of a nucleic acid inserted therein.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" includes reference to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence, a gap penalty is typically introduced and is subtracted from the number of matches.

Methods of alignment of sequences for comparison are well-known in the art. Optimal alignment of sequences for comparison may be conducted by the local homology algorithm of Smith and Waterman, *Adv. Appl. Math.* 2:482 (1981); by the homology alignment algorithm of Needleman and Wunsch, *J. Mol. Biol.* 48:443 (1970); by the search for similarity method of Pearson and Lipman, *Proc. Natl. Acad. Sci.* 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, *Gene* 73:237-244 (1988); Higgins and Sharp, CABIOS 5:151-153 (1989); Corpet, et al., *Nucleic Acids Research* 16:10881-90 (1988); Huang, et al., *Computer Applications in the Biosciences* 8:155-65 (1992), and Pearson, et al., *Methods in Molecular Biology* 24:307-331 (1994). The BLAST family of programs which can be used for database similarity searches includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, *Current Protocols in Molecular Biology*, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., *Nucleic Acids Res.* 25:3389-3402 (1997). Software for performing BLAST analyses is publicly available, e.g., through the National Center for Biotechnology-Information www.ncbi.nlm.nih.gov). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) *Proc. Natl. Acad. Sci. USA* 89:10915).

In addition to calculating percent sequence identity, the BLAST algorithm also performs a statistical analysis of the similarity between two sequences (see, e.g., Karlin & Altschul, *Proc. Natl. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance.

BLAST searches assume that proteins can be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs can be employed to reduce such low-complexity alignments. For example, the SEG (Wooten and Federhen, *Comput. Chem.*, 17:149-163 (1993)) and XNU (Claverie and States, *Comput. Chem.*, 17:191-201 (1993)) low-complexity filters can be employed alone or in combination.

(c) As used herein, "sequence identity" or "identity" in the context of two nucleic acid or polypeptide sequences includes reference to the residues in the two sequences which are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences which differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, *Computer Applic. Biol. Sci.*, 4:11-17 (1988) e.g., as implemented in the program PC/GENE (Intelligenetics, Mountain View, Calif., USA).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

(e) The term "substantial identity" of polynucleotide sequences means that a polynucleotide comprises a sequence that has at least 70% sequence identity, preferably at least 80%, more preferably at least 90% and most preferably at least 95%, compared to a reference sequence using one of the alignment programs described using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, ore preferably at least 70%, 80%, 90%, and most preferably at least 95%.

Another indication that nucleotide sequences are substantially identical is if two molecules hybridize to each other under stringent conditions. However, nucleic acids which do not hybridize to each other under stringent conditions are still substantially identical if the polypeptides which they encode are substantially identical. This may occur, e.g., when a copy of a nucleic acid is created using the maximum codon degeneracy permitted by the genetic code. One indication that two nucleic acid sequences are substantially identical is that the polypeptide which the first nucleic acid encodes is immunologically cross reactive with the polypeptide encoded by the second nucleic acid.

(e) The terms "substantial Identity" in the context of a peptide indicates that a peptide comprises a sequence with at least 70% sequence identity to a reference sequence, preferably 80%, ore preferably 85%, most preferably at least 90% or 95% sequence identity to the reference sequence over a specified comparison window. Optionally, optimal alignment is conducted using the homology alignment algorithm of Needleman and Wunsch, *J. Mol. Biol.* 48:443 (1970). an indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions which are not identical may differ by conservative amino acid changes.

A, In vitro interaction between the CC domain and the putative Rps1-k-2-interactors.

B, In vitro interaction between the NB domain and the putative Rps1-k-2-interactors.

C, In vitro interaction between the CC-NB domain and the putative Rps1-k-2-interactors. In the first lane, the TNT translational reaction mix and the CC domain of Rps1-k-2 as negative control.

In the last lane, the TNT translational reaction mix and the CC-NB domain of Rps1-k-2 as negative control.

Predicted sizes of the baits are: CC domain, ~17 kDa; NB, ~42 kDa and CC-NB, ~58 kDa.

FIG. 4. RNA interference (RNAi) of candidate Rps1-k-2-interactors. All the RNAi constructs of independent Rps1-k-2-interactor were transformed into Williams 82 cotyledons. A, RNAi of putative Rps1-k-2-interactors resulted in the loss of Rps1-k encoded *Phytophthora* resistance. Here we showed only a representative one. pART27GFP/W82, cotyledons of Williams 82 transformed with empty vector; pART27GFP/W, cotyledons of Williams transformed with empty vector; pART27GFP_RIP11/W82, cotyledons of Williams 82 transformed with RIP11 RNAi construct; pART27GFP_RIP13/W82, cotyledons of Williams 82 transformed with RIP13 RNAi construct. B, Summary of RNAi effects on Rps1-k-2-mediated resistance of candidate Rps1-k-2-interactors. The data presented are a summary of results from 3 to 6 independent experiments. On the average 10-15 cotyledons/construct were evaluated in each experiment.

FIG. 5. RIP13 is a type II metacaspase. A. Predicted protein sequence of RIP13. The underlined part is the sequence used in the yeast two-hybrid screen. B. RIP13 consists of a p20 caspase-like subunit, a linker region and a p10 caspase-like subunit. The predicted catalytic cystein (C139) and the auto-cleavage sites Argine (R187) and lysine (K271) are indicated.

FIG. 6. Reduced steady state RIP13 transcript levels following RNAi in soybean cotyledons. RNA was isolated from cotyledons carrying the RIP13 silencing construct or only the empty vector. The samples in the right and left panels were from two independent experiments. Soybean actin1 gene was amplified as an internal control to standardize the total RNA level of each sample used for RT-PCR.

FIG. 7. Induction of RIP13 transcripts following *P. sojae* infection. RNA was isolated from avirulent *P. sojae* race 18 infected etiolated Williams 82 hypocotyls. Infected tissue samples were harvested at indicated hours post inoculation (hpi). Soybean Actin1 gene was amplified as an internal control to standardize the RNA levels among the samples. –, controls without reverse transcriptase; +, with reverse transcriptase enzyme.

FIG. 8. Alignment of deduced protein sequences of RIP6 and two soybean homologs. The two soybean homologs of RIP6 were identified by querying the soybean EST database with the RIP6 sequence. The alignment was obtained using ClustalW at www.align.genome.jp.

Figure 9:
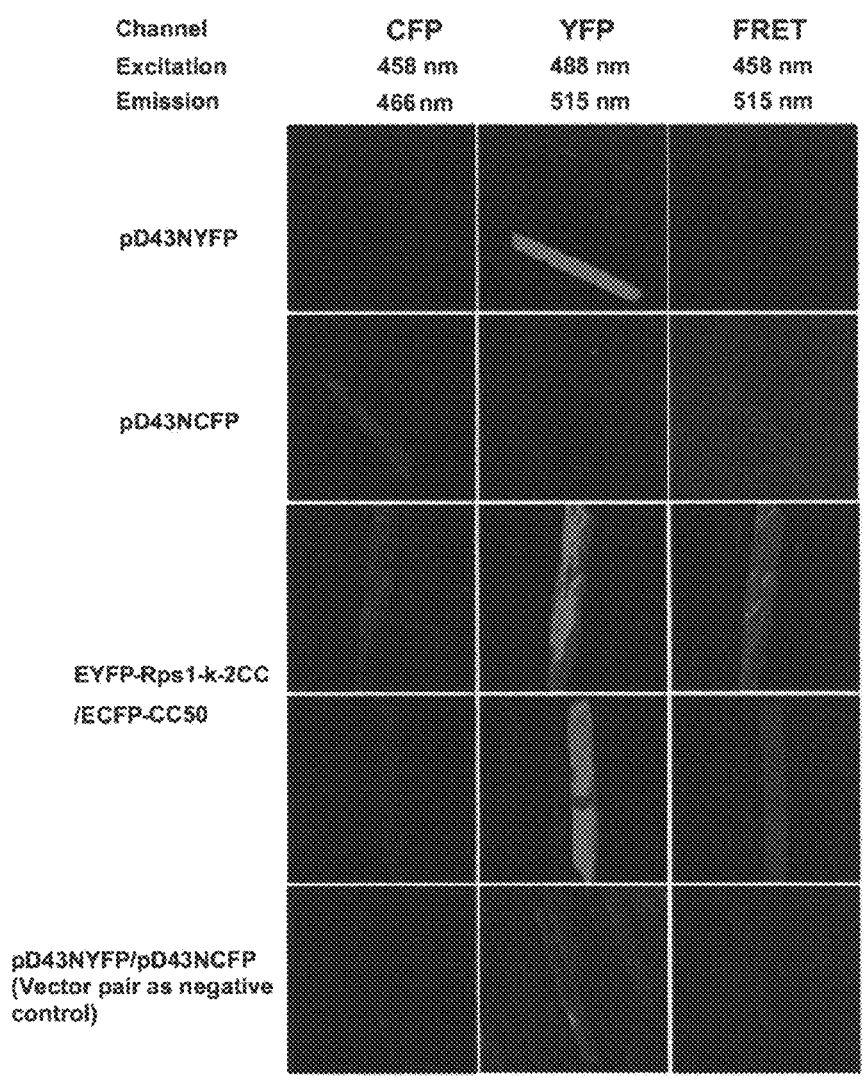

FIG. 9. In vivo interaction between GmMcII and Rps1-k-2-CC. FRET was performed by transient co-expressing ECFP-GmMcII-C(CC50 fused to ECFP) and EYFP-Rps1-k-2CC (coiled coil domain of Rps1-k-2 fused to EYFP) fusion proteins in etiolated soybean hypocotyls by particle bombardment method. The pD43NCFP (ECFP) and pD43NYFP (EYFP) vectors were used as negative controls. Fluorescence was detected by confocal microscope. The fluorescence signals were falsely colored.

Figure 10:
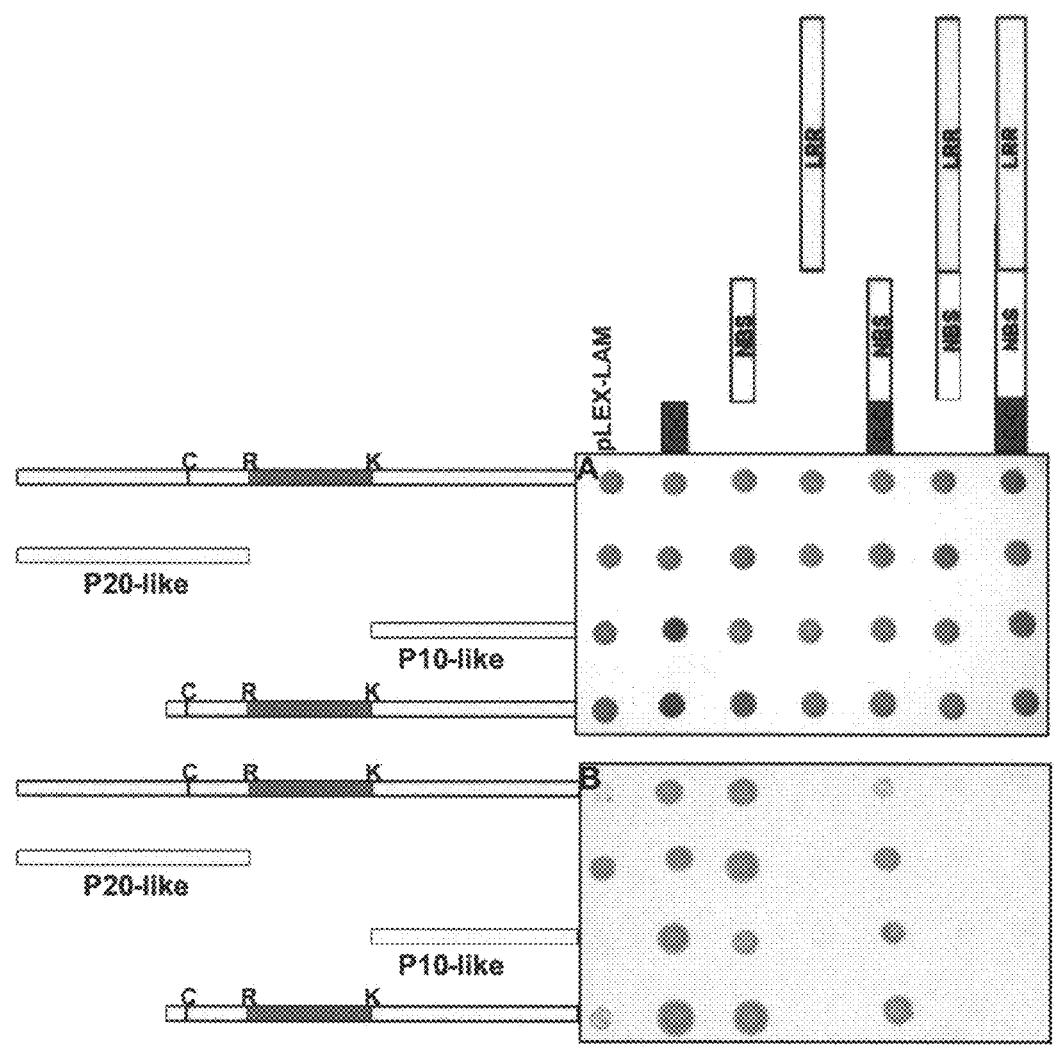

FIG. 10. P10 caspase-like subunit of GmMcII interacts with Rps1-k-2 coiled coil domain. Yeast colonies carrying combinations of GmMcII and its sub units with Rps1-k-2 and its domains and domain combinations were plated on SD plates containing: A) X-gal but no uracil, histidine and tryptophan; and B) no uracil, histidine, tryptophan and leucine. Colonies were individually suspended in 10 µl sterile water, of which 1 µl spotted onto the plates. Three individual domains of Rps1-k-2: (i) C-C, the N-terminal CC domain; (ii) NBS, the NB-ARC domain; and (iii) LRR, the C-terminal LRR domain, as well as two domain combinations: (i) C-C NBS, CC and NB-ARC domain combination; and (ii) NBS LRR, NB-ARC and LRR domain combination; and Rps1-k-2 ORF previously cloned into pLexA vector for screening the prey cDNA library were utilized in studying their in vivo interactions with GmMcII. GmMcII ORF, p20, p10, and CC50 cloned into the pB42AD vector were used in the interaction studies. pLEX-LAM, 400 bp human Lamin C protein in pLexA vector served as the negative control.

Figure 11:
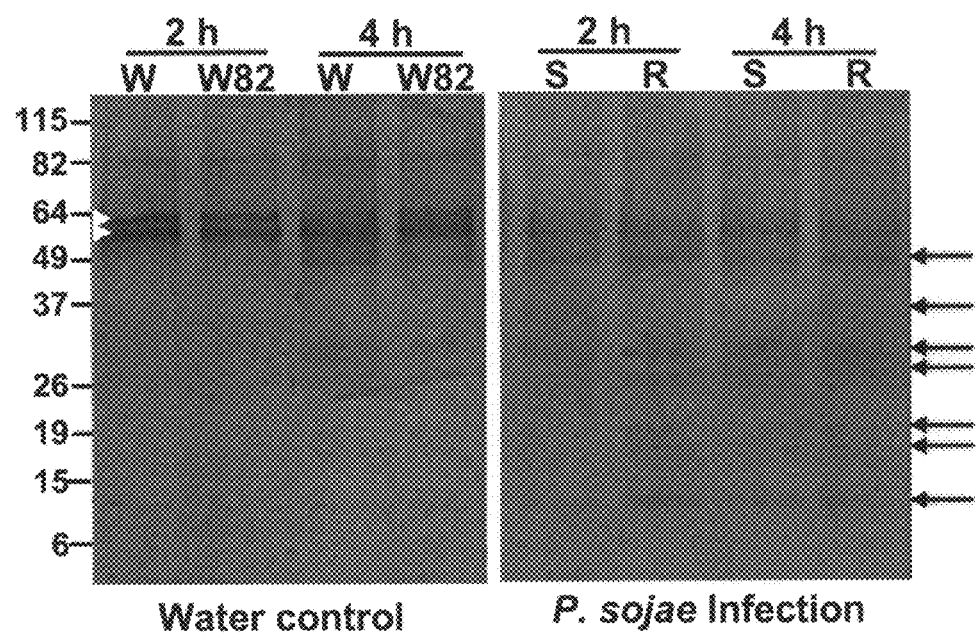

FIG. 11. GmMcII is processed in infected hypocotyl tissues. Etiolated hypocotyls of 7-day old seedlings were inoculated with *P. sojae* zoospore or H$_2$0 droplets, and thin tissue sections just beneath the zoospore or water droplets were excised two and four hours following infection or H$_2$0 droplet treatment. Tissues were immediately frozen in liquid N$_2$ and processed for western blotting using the anti-mcII-Pa antibody. W, Williams (susceptible to *P. sojae*); W82, Williams 82 (carries Rps1-k-2 and resistant to *P. sojae*); S, susceptible to *P. sojae*; R, resistant to *P. sojae*. Williams produced susceptible response and Williams 82 produced resistant response following infection with *P. sojae* (Lanes 5-8). Note that two protein bands, strongly hybridized to the antibody in water controls (lanes 1 to 4), were rapidly processed following infection (Lanes 5 to 8). Anti-mcII-Pa antibody hybridized to the *E. coli*-expressed GmMcII protein (data not shown).

FIG. 12. FIG. 12 depicts the sequences of the invention.

DETAILED DESCRIPTION OF THE INVENTION

The present invention provides, inter alia, compositions and methods for promoting pathogen resistance in plants, more particularly for improving *Phytophthora* resistance of susceptible plants. The compositions of the invention relate to the metacaspase type II encoding sequences which are induced upon *Phytophthora sojae* infection and are silenced in cotyledons with susceptibility to *Phytophthora*. Thus the metacaspase type II nucleic acid molecules may be modulated to confer improved *Phytophthora* resistance in soybeans. These compositions can be transferred into plants to confer or improve *Phytophthora* resistance, modified to engineer gene sequences for broad based non specific resistance in plants, or to isolate and identify alternate gene forms and markers which may be used in breeding regimes. By "confer or improve *Phytophthora* or other such pathogen resistance" is intended that the proteins or sequences, either alone or in combination with other proteins or sequences, enhance resistance of a plant to *Phytophthora* and *Phytophthora*-caused damage or to other pathogens which cause a similar plant reaction. In this manner, resistance to these fungal pathogens and other pathogens such as *Pseudomonas syringae* pv. *glycinea* (Psg), soybean cyst nematode (SCN), or soybean mosaic virus (SMV) can be enhanced or improved in the transformed plant or its progeny when at least one of the sequences of the invention is modulated according to the invention.

The compositions include nucleic acid molecules comprising sequences of plant genes and the polypeptides encoded thereby. Particularly, the nucleotide and amino acid sequence for a novel metacaspase type II protein which is associated with Rps1-k-2 mediated resistance to *Phytophthora* infection has been isolated. As discussed in more detail below, the sequences of the invention are presumably involved in many basic biochemical pathways that regulate plant pathogen resistance. Thus, methods are provided for the modulation of these sequences in a host plant to improve plant defense responses. Some of the methods involve stably transforming a plant with a nucleotide sequence of the invention operably linked with a promoter capable of driving expression of a gene in a plant cell other methods may involved inhibition of the same sequences to confer improved pathogen resistance in a particular plant.

Promoter and other regulatory elements which are natively associated with these genes can be easily isolated using the sequences and methods described herein with no more than routine experimentation. These sequences can also be used to identify promoter, enhancer or other signaling sequences in the regulatory regions of pathogen resistance genes. Such regulatory elements or promoters would provide for temporal and spatial expression of operably linked sequences with pathogen infection in a plant. Nucleotide sequences operably linked to such promoter sequences are transformed into a plant cell. Exposure of the transformed plant to a stimulus such as pathogen infection could induce transcriptional activation of the nucleotide sequences operably linked to these promoter regulatory sequences.

Transformed plants can be obtained having altered or enhanced responses to fungal pathogen attack; hence, the methods and compositions may find uses in altering the response of plants to similar stresses as well. Thus, the sequences of the invention find use in engineering broad-spectrum disease and pest resistance in a variety of plants. A polypeptide is said to modulate Rps1-k activity when it affects one or more of the properties of the native protein. It is within the skill in the art to assay protein activities obtained from various sources to determine whether the properties of the proteins are the same. In so doing, one of skill in the art may employ any of a wide array of known assays including, for example, biochemical and/or pathological assays. For example, one of skill in the art could readily produce a plant transformed with a metacaspase polypeptide variant and assay a property of native metacaspase or Rps1-k protein in that plant material to determine whether a particular Rps1-k or metacaspase property was retained by the variant.

The compositions and methods of the invention are presumably involved in biochemical pathways and as such may also find use in the activation or modulation of expression of other genes, including those involved in other aspects of pathogen response.

By "modulating" or "modulation" is intended that the level of expression of a gene may be increased or decreased relative to genes driven by other promoters or relative to the normal or uninduced level of the gene in question.

The present invention provides for isolated nucleic acid molecules comprising nucleotide sequences encoding the amino acid sequence shown in the Figures attached (see examples 2 and 4) and their conservatively modified variants. Further provided are polypeptides having an amino acid sequence encoded by a nucleic acid molecule described herein, for example those polypeptides comprising the sequences set forth in the figures herein, and fragments and variants thereof.

The invention encompasses isolated or substantially purified nucleic acid or protein compositions. An "isolated" or "purified" nucleic acid molecule or protein, or biologically active portion thereof, is substantially free of other cellular material, or culture medium when produced by recombinant techniques, or substantially free of chemical precursors or other chemicals when chemically synthesized. In some embodiments, an "isolated" nucleic acid is free of sequences (such as other protein-encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, 0.4 kb, 0.3 kb, 0.2 kb, or 0.1 kb, or 50, 40, 30, 20, or 10 nucleotides that naturally flank the nucleic acid molecule in genomic DNA of the cell from which the nucleic acid is derived. A protein that is substantially free of cellular material includes preparations of protein having less than about 30%, 20%, 10%, 5%, (by dry weight) of contaminating protein. When the protein of the invention or biologically active portion thereof is recombinantly produced, culture medium may represent less than about 30%, 20%, 10%, or 5% (by dry weight) of chemical precursors or non-protein-of-interest chemicals.

Fragments and variants of the disclosed nucleotide sequences are encompassed by the present invention. Fragments and variants of proteins encoded by the disclosed nucleotide sequences are also encompassed by the present invention. By "fragment" is intended a portion of the nucleotide sequence or a portion of the amino acid sequence and hence protein encoded thereby. Fragments of a nucleotide sequence may encode protein fragments that retain the biological activity of the native protein and hence affect development, developmental pathways, stress responses, and/or disease resistance by retaining Rps1-k-like activity. Alternatively, fragments of a nucleotide sequence that are useful as hybridization probes generally do not encode fragment proteins retaining biological activity. Thus, fragments of a nucleotide sequence may range from at least about 20 nucleotides, about 50 nucleotides, about 100 nucleotides, and up to the full-length nucleotide sequence encoding the proteins of the invention.

A fragment of a metacaspase nucleotide sequence that encodes a biologically active portion of a metacaspase protein of the invention will encode at least 12, 25, 30, 50, 75, etc. contiguous amino acids, or up to the total number of amino acids present in a full-length metacaspase protein of the invention.

Fragments of a metacaspase nucleotide sequence that are useful as hybridization probes or PCR primers generally may or may not encode a biologically active portion of a protein. Thus, a fragment of a metacaspase nucleotide sequence may encode a biologically active portion of a metacaspase protein, or it may be used as a hybridization probe or PCR primer using methods disclosed below. A biologically active portion of a metacaspase protein can be prepared by isolating a portion of the Rps1-k nucleotide sequences of the invention, expressing the encoded portion of the Rps1-k protein (e.g., by recombinant expression in vitro), and assessing the activity of the encoded portion of the Metacaspase protein. Nucleic acid molecules that are fragments of an Metacaspase nucleotide sequence comprise at least 16, 20, 25, 30, 40, 50, 60, 70, 80, 90, 100, 125, 150, 175, 200, etc. nucleotides, or up to the number of nucleotides present in a full-length Metacaspase nucleotide sequences disclosed herein.

The proteins of the invention may be altered in various ways including amino acid substitutions, deletions, truncations, and insertions. Methods for such manipulations are generally known in the art. For example, amino acid sequence variants of the Metacaspase proteins can be prepared by mutations in the DNA. Methods for mutagenesis and nucleotide sequence alterations are well known in the art. See, for example, Kunkel (1985) *Proc. Nat. Acad. Sci. USA* 82:488-492; Kunkel et al. (1987) *Methods in Enzymol.* 154:367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff et al. (1978) *Atlas of Protein Sequence and Structure* (Natl. Biomed. Res. Found., Washington, D. C.), herein incorporated by reference. Conservative substitutions, such as exchanging one amino acid with another having similar properties, may be made.

It is recognized that having identified the nucleotide sequences disclosed herein, it is within the state of the art to isolate and identify regulatory elements in the 5' untranslated region upstream from regions defined herein. Thus for example, the promoter regions of the gene sequences disclosed herein may further comprise upstream regulatory elements that confer tissue-preferred expression of heterologous nucleotide sequences operably linked to the disclosed promoter sequence. See particularly, Australian Patent No. AU-A-77751/94 and U.S. Pat. Nos. 5,466,785 and 5,635,618. It is also recognized by those of skill in the art that regulatory elements may be found in transcribed regions of a gene, for example in the region between transcription start and translation start as well as 3' to the end of translation; such elements may be found in the sequences set forth herein.

The nucleotide sequences of the invention can be used to isolate corresponding sequences from other organisms, particularly other plants, more particularly other crop plants. In this manner, methods such as PCR, hybridization, and the like can be used to identify such sequences based on their sequence homology to the sequences set forth herein. Sequences isolated based on their sequence identity to the nucleotide sequences set forth herein or to fragments thereof are encompassed by the present invention. Such sequences include sequences that are orthologs of the disclosed sequences. By "orthologs" is intended genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species. Thus, isolated sequences that have Metacaspase-like activity or and which hybridize under stringent conditions to the Metacaspase sequences disclosed herein, or to fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook et al. (1989) *Molecular Cloning: A Laboratory Manual* (2d ed., Cold Spring Harbor Laboratory Press Plainview, N. Y.). See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present it a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}$P, or any other detectable marker. Thus, for example, probes for hybridization can be made by labeling synthetic oligonucleotides based on the disease-resistant sequences of the invention. Methods for preparation of probes for hybridization and for construction of cDNA and genomic libraries are generally known in the art and are disclosed in Sambrook et al. (1989) *Molecular Cloning: A Laboratory Manual* (2d ed., Cold Spring Harbor Laboratory Press, Plainview, N. Y.).

For example, an entire sequence disclosed herein, or one or more portions thereof, may be used as a probe capable of specifically hybridizing to corresponding *Phytophthora*-response sequences, including promoters and messenger RNAs. To achieve specific hybridization under a variety of conditions, such probes include sequences that are unique among *Phytophthora*-response sequences and may be at least about 10 or 15 or 17 nucleotides in length or at least about 20 or 22 or 25 nucleotides in length. Such probes may be used to amplify corresponding sequences from a chosen organism by PCR. This technique may be used to isolate additional coding sequences from a desired organism or as a diagnostic assay to determine the presence of coding sequences in an organism. Hybridization techniques include hybridization screening of plated DNA libraries (either plaques or colonies; see, for example, Sambrook et al. (1989) *Molecular Cloning: A Laboratory Manual* (2d ed., Cold Spring Harbor Laboratory Press, Plainview, N. Y.).

Assays that measure antipathogenic activity induced by the signal pathway from the sequences herein are commonly known in the art, as are methods to quantitate disease resistance in plants following pathogen infection. See, for example, U.S. Pat. No. 5,614,395, herein incorporated by reference. These assays may be used to measure the activity of the polypeptides of the invention. Such techniques include, measuring over time, the average lesion diameter, the pathogen biomass, and the overall percentage of decayed plant tissues. For example, a plant either expressing an antipathogenic polypeptide or having an antipathogenic composition applied to its surface shows a decrease in tissue necrosis (i.e., lesion diameter) or a decrease in plant death following pathogen challenge when compared to a control plant that was not exposed to the antipathogenic composition. Alternatively, antipathogenic activity can be measured by a decrease in pathogen biomass. For example, a plant expressing an antipathogenic polypeptide or exposed to an antipathogenic composition is challenged with a pathogen of interest. Over time, tissue samples from the pathogen-inoculated tissues are obtained and RNA is extracted. The percent of a specific pathogen RNA transcript relative to the level of a plant specific transcript allows the level of pathogen biomass to be determined. See, for example, Thomma et al. (1998) *Plant Biology* 95:15107-15111, herein incorporated by reference.

Furthermore, in vitro antipathogenic assays include, for example, the addition of varying concentrations of the antipathogenic composition to paper disks and placing the disks on agar containing a suspension of the pathogen of interest. Following incubation, clear inhibition zones develop around the discs that contain an effective concentration of the antipathogenic polypeptide (Liu et al. (1994) *Plant Biology* 91:1888-1892, herein incorporated by reference). Additionally, microspectrophotometrical analysis can be used to measure the in vitro antipathogenic properties of a composition (Hu et al. (1997) *Plant Mol. Biol.* 34:949-959 and Cammue et al. (1992) *J. Biol. Chem.* 267: 2228-2233, both of which are herein incorporated by reference).

Pathogens of the invention include, but are not limited to, fungal and viral pathogens for primarily soybeans which include: *Phytophthora sojae, Macrophomina phaseolina, Rhizoctonia solani, Sclerotinia sclerotiorum, Fusarium virguliformae, Diaporthe phaseolorum* var. *sojae* (*Phomopsis sojae*), *Diaporthe phaseolorum* var. *caulivora, Sclerotium rolfsii, Cercospora kikuchii, Cercospora sojina, Peronospora manshurica, Colletotrichum dematium* (*Colletotichum truncatum*), *Corynespora cassfcola, Septoria glycines, Phyllosticta sojicola, Alternaria alternata, Pseudomonas syringae* p.v. *glycinea, Xanthomonas campestris* p.v. *phaseoli, Microsphaera diffusa, Fusarium semitectum, Phialophora gregata*, Soybean mosaic virus, *Glomerella glycines*, Tobacco Ring spot virus, Tobacco Streak virus, *Phakopsora pachyrhizi, Pythium aphanidermatum, Pythium ultimum, Pythium debaryanum*, Tomato spotted wilt virus, *Heterodera glycines*.

It is understood in the art that plant DNA viruses and fungal pathogens remodel the control of the host replication and gene expression machinery to accomplish their own replication and effective infection. The plant response to stress, such as stress caused by *Phytophthora* attack, is known to involve many basic biochemical pathways and cellular functions. Hence, the sequences of the invention may find use in altering the defense mechanisms of a host plant to provide broad-based resistance to disease or insect pests. Additionally, the present invention may be useful in preventing corruption of the cell machinery by viruses and other plant pathogens.

The compositions and methods of the invention function to inhibit or prevent plant diseases. The gene products may accomplish their anti-pathogenic effects by suppressing, controlling, and/or killing the invading pathogenic organism through activation of a signal pathway leading to accumulation of defense compounds.

The cells that have been transformed may be grown into plants in accordance with conventional ways. See, for example, McCormick et al. (1986) *Plant Cell Reports* 5:8184. These plants may then be grown, and either pollinated with the same transformed strain or different strains, and the resulting hybrid having constitutive expression of the desired phenotypic characteristic identified. Two or more generations may be grown to ensure that constitutive expression of the desired phenotypic characteristic is stably maintained and inherited and then seeds harvested to ensure constitutive expression of the desired phenotypic characteristic has been achieved.

The invention in one aspect comprises expression constructs comprising a DNA sequence which encodes upon expression an Metacaspase gene product operably linked to a promoter to direct expression of the protein. These constructs are then introduced into plant cells using standard molecular biology techniques. The invention can be also be used for hybrid plant or seed production, once transgenic inbred parental lines have been established.

In another aspect the invention involves the inhibition of the regulatory gene product in plants through introduction of a construct designed to inhibit the same gene product. The design and introduction of such constructs based upon known DNA sequences is known in the art and includes such technologies as antisense RNA or DNA, co-suppression or any other such mechanism. Several of these mechanisms are described and disclosed in U.S. Pat. No. 5,686,649 to Chua et. al, which is hereby expressly incorporated herein by reference.

The methods of the invention described herein may be applicable to any species of plant.

Production of a genetically modified plant tissue either expressing or inhibiting expression of a structural gene combines the teachings of the present disclosure with a variety of techniques and expedients known in the art. In most instances, alternate expedients exist for each stage of the overall process. The choice of expedients depends on the variables such as the plasmid vector system chosen for the cloning and introduction of the recombinant DNA molecule, the plant species to be modified, the particular structural gene, promoter elements and upstream elements used. Persons skilled in the art are able to select and use appropriate alternatives to achieve functionality. Culture conditions for expressing desired structural genes and cultured cells are known in the art. Also as known in the art, a number of both monocotyledonous and dicotyledonous plant species are transformable and regenerable such that whole plants containing and expressing desired genes under regulatory control of the promoter molecules according to the invention may be obtained. As is known to those of skill in the art, expression in transformed plants may be tissue specific and/or specific to certain developmental stages. Truncated promoter selection and structural gene selection are other parameters which may be optimized to achieve desired plant expression or inhibition as is known to those of skill in the art and taught herein.

The following is a non-limiting general overview of Molecular biology techniques which may be used in performing the methods of the invention.

Promoters

The constructs, promoters or control systems used in the methods of the invention may include a tissue specific promoter, an inducible promoter or a constitutive promoter.

A large number of suitable promoter systems are available. For example one constitutive promoter useful for the invention is the cauliflower mosaic virus (CaMV) 35S. It has been shown to be highly active in many plant organs and during many stages of development when integrated into the genome of transgenic plants and has been shown to confer expression in protoplasts of both dicots and monocots.

Organ-specific promoters are also well known. For example, the E8 promoter is only transcriptionally activated during tomato fruit ripening, and can be used to target gene expression in ripening tomato fruit (Deikman and Fischer, *EMBO J.* (1988) 7:3315; Giovannoni et al., *The Plant Cell* (1989) 1:53). The activity of the E8 promoter is not limited to tomato fruit, but is thought to be compatible with any system wherein ethylene activates biological processes. Similarly the Lipoxegenase ("the LOX gene") is a fruit specific promoter.

Other fruit specific promoters are the 1.45 promoter fragment disclosed in Bird, et al., *Plant Mol. Bio.*, pp 651-663 (1988) and the polygalacturonase promoter from tomato disclosed in U.S. Pat. No. 5,413,937 to Bridges et al.

Leaf specific promoters include as the AS-1 promoter disclosed in U.S. Pat. No. 5,256,558 to Coruzzi and the RBCS-3A promoter isolated from pea the RBCS-3A gene disclosed in U.S. Pat. No. 5,023,179 to Lam et al.

And finally root specific promoters include the CamV 35S promoter disclosed in U.S. Pat. No. 391,725 to Coruzzi et al; the RB7 promoter disclosed in U.S. Pat. No. 5,459,252 to Conking et al and the promoter isolated from *Brassica napus* disclosed in U.S. Pat. No. 5,401,836 to Bazczynski et al. which give root specific expression.

Other examples of promoters include maternal tissue promoters such as seed coat, pericarp and ovule. Promoters highly expressed early in endosperm development are most effective in this application. Of particular interest is the promoter from the a' subunit of the soybean β-conglycinin gene [Walling et al., *Proc. Natl. Acad. Sci. USA* 83:2123-2127 (1986)] which is expressed early in seed development in the endosperm and the embryo.

Further seed specific promoters include the Napin promoter described in U.S. Pat. No. 5,110,728 to Calgene, which describes and discloses the use of the napin promoter in directing the expression to seed tissue of an acyl carrier protein to enhance seed oil production; the DC3 promoter from carrots which is early to mid embryo specific and is disclosed at *Plant Physiology*, October 1992 100(2) p. 576-581, "Hormonal and Environmental Regulation of the Carrot Lea-class Gene Dc 3, and *Plant Mol. Biol., April* 1992, 18(6) p. 1049-1063, "Transcriptional Regulation of a Seed Specific Carrot Gene, DC 8": the phaseolin promoter described in U.S. Pat. No. 5,504,200 to Mycogen which discloses the gene sequence and regulatory regions for phaseolin, a protein isolated from *P. vulgaris* which is expressed only while the seed is developing within the pod, and only in tissues involved in seed generation.

Other organ-specific promoters appropriate for a desired target organ can be isolated using known procedures. These control sequences are generally associated with genes uniquely expressed in the desired organ. In a typical higher plant, each organ has thousands of mRNAs that are absent from other organ systems (reviewed in Goldberg, Phil, *Trans. R. Soc. London* (1986) B314-343. mRNAs are first isolated to obtain suitable probes for retrieval of the appropriate genomic sequence which retains the presence of the natively associated control sequences. An example of the use of techniques to obtain the cDNA associated with mRNA specific to avocado fruit is found in Christoffersen et al., *Plant Molecular Biology* (1984) 3:385. Briefly, mRNA was isolated from ripening avocado fruit and used to make a cDNA library. Clones in the library were identified that hybridized with labeled RNA isolated from ripening avocado fruit, but that did not hybridize with labeled RNAs isolated from unripe avocado fruit. Many of these clones represent mRNAs encoded by genes that are transcriptionally activated at the onset of avocado fruit ripening.

Another very important method that can be used to identify cell type specific promoters that allow even to identification of genes expressed in a single cell is enhancer detection (O'Kane, C., and Gehring, W. J. (1987), "Detection in situ of genomic regulatory elements in *Drosophila*", *Proc. Natl. Acad. Sci. USA*, 84, 9123-9127). This method was first developed in *Drosophila* and rapidly adapted to mice and plants (Wilson, C., Pearson, R. K., Bellen, H. J., O'Kane, C. J., Grossniklaus, U., and Gehring, W. J. (1989), "P-element-mediated enhancer detection: an efficient method for isolating and characterizing developmentally regulated genes in *Drosophila*", *Genes & Dev.*, 3, 1301-1313; Skarnes, W. C. (1990), "Entrapment vectors: a new tool for mammalian genetics", *Biotechnology*, 8, 827-831; Topping, J. F., Wei, W., and Lindsey, K. (1991), "Functional tagging of regulatory elements in the plant genome", *Development*, 112, 1009-1019; Sundaresan, V., Springer, P. S., Volpe, T., Haward, S., Jones, J. D. G., Dean, C., Ma, H., and Martienssen, R. A., (1995), "Patterns of gene action in plant development revealed by enhancer trap and gene trap transposable elements", *Genes & Dev.*, 9, 1797-1810).

The promoter used in the method of the invention may be an inducible promoter. An inducible promoter is a promoter that is capable of directly or indirectly activating transcription of a DNA sequence in response to an inducer. In the absence of an inducer, the DNA sequence will not be transcribed. Typically, the protein factor that binds specifically to an inducible promoter to activate transcription is present in an inactive form which is then directly or indirectly converted to the active form by the inducer. The inducer may be a chemical agent such as a protein, metabolite (sugar, alcohol etc.), a growth regulator, herbicide, or a phenolic compound or a physiological stress imposed directly by heat, salt, toxic elements etc. or indirectly through the action of a pathogen or disease agent such as a virus. A plant cell containing an inducible promoter may be exposed to an inducer by externally applying the inducer to the cell such as by spraying, watering, heating, or similar methods. Examples of inducible promoters include the inducible 70 kd heat shock promoter of *D. melanogaster* (Freeling, M., Bennet, D. C., Maize ADN 1, *Ann. Rev. of Genetics,* 19:297-323) and the alcohol dehydrogenase promoter which is induced by ethanol (Nagao, R. T., et al., Miflin, B. J., Ed. Oxford Surveys of Plant Molecular and Cell Biology, Vol. 3, p. 384-438, Oxford University Press, Oxford 1986) or the Lex A promoter which is triggered with chemical treatment and is available through Ligand pharmaceuticals. The inducible promoter may be in an induced state throughout seed formation or at least for a period which corresponds to the transcription of the DNA sequence of the recombinant DNA molecule(s).

Another example of an inducible promoter is the chemically inducible gene promoter sequence isolated from a 27 kd subunit of the maize glutathione-S-transferase (GST II) gene. Two of the inducers for this promoter are N,N-diallyl-2,2-dichloroacetamide (common name: dichloramid) or benzyl-=2-chloro-4-(trifluoromethyl)-5-thiazolecarboxylate (common name: flurazole). In addition, a number of other potential inducers may be used with this promoter as described in published PCT Application No. PCT/GB90/00110 by ICI.

Another example of an inducible promoter is the light inducible chlorophyll a/b binding protein (CAB) promoter, also described in published PCT Application No. PCT/GB90/00110 by ICI.

Inducible promoters have also been described in published Application No. EP89/103888.7 by Ciba-Geigy. In this application, a number of inducible promoters are identified, including the PR protein genes, especially the tobacco PR protein genes, such as PR-1a, PR-1b, PR-1c, PR-1, PR-A, PR-S, the cucumber chitinase gene, and the acidic and basic tobacco beta-1,3-glucanase genes. There are numerous potential inducers for these promoters, as described in Application No. EP89/103888.7.

The preferred promoters may be used in conjunction with naturally occurring flanking coding or transcribed sequences of the feronia regulatory genes or with any other coding or transcribed sequence that is critical to pollin tube formation and/or fertilization.

It may also be desirable to include some intron sequences in the promoter constructs since the inclusion of intron sequences in the coding region may result in enhanced expression and specificity. Thus, it may be advantageous to join the DNA sequences to be expressed to a promoter sequence that contains the first intron and exon sequences of a polypeptide which is unique to cells/tissues of a plant critical to female gametophyte development and/or function.

Additionally, regions of one promoter may be joined to regions from a different promoter in order to obtain the desired promoter activity resulting in a chimeric promoter. Synthetic promoters which regulate gene expression may also be used.

The expression system may be further optimized by employing supplemental elements such as transcription terminators and/or enhancer elements.

Other Regulatory Elements

In addition to a promoter sequence, an expression cassette or construct should also contain a transcription termination region downstream of the structural gene to provide for efficient termination. The termination region or polyadenylation signal may be obtained from the same gene as the promoter sequence or may be obtained from different genes. Polyadenylation sequences include, but are not limited to the *Agrobacterium* octopine synthase signal (Gielen et al., *EMBO J.* (1984) 3:835-846) or the nopaline synthase signal (Depicker et al., *Mol. and Appl. Genet.* (1982) 1:561-573).

Marker Genes

Recombinant DNA molecules containing any of the DNA sequences and promoters described herein may additionally contain selection marker genes which encode a selection gene product which confer on a plant cell resistance to a chemical agent or physiological stress, or confers a distinguishable phenotypic characteristic to the cells such that plant cells transformed with the recombinant DNA molecule may be easily selected using a selective agent. One such selection marker gene is neomycin phosphotransferase (NPT II) which confers resistance to kanamycin and the antibiotic G-418. Cells transformed with this selection marker gene may be selected for by assaying for the presence in vitro of phosphorylation of kanamycin using techniques described in the literature or by testing for the presence of the mRNA coding for the NPT II gene by Northern blot analysis in RNA from the tissue of the transformed plant. Polymerase chain reactions are also used to identify the presence of a transgene or expression using reverse transcriptase PCR amplification to monitor expression and PCR on genomic DNA. Other commonly used selection markers include the ampicillin resistance gene, the tetracycline resistance and the hygromycin resistance gene. Transformed plant cells thus selected can be induced to differentiate into plant structures which will eventually yield whole plants. It is to be understood that a selection marker gene may also be native to a plant.

Transformation

Numerous methods for plant transformation have been developed, including biological and physical, plant transformation protocols. See, for example, Miki et al., "Procedures for Introducing Foreign DNA into Plants" in *Methods in Plant Molecular Biology and Biotechnology*, Glick, B. R. and Thompson, J. E. Eds. (CRC Press, Inc., Boca Raton, 1993) pages 67-88. In addition, expression vectors and in vitro culture methods for plant cell or tissue transformation and regeneration of plants are available. See, for example, Gruber et al., "Vectors for Plant Transformation" in *Methods in Plant Molecular Biology and Biotechnology*, Glick, B. R. and Thompson, J. E. Eds. (CRC Press, Inc., Boca Raton, 1993) pages 89-119.

A. *Agrobacterium*-Mediated Transformation

One method for introducing an expression vector into plants is based on the natural transformation system of *Agrobacterium*. See, for example, Horsch et al., *Science* 227: 1229 (1985). *A. tumefaciens* and *A. rhizogenes* are plant pathogenic soil bacteria which genetically transform plant cells. The Ti and Ri plasmids of *A. tumefaciens* and *A. rhizogenes*, respectively, carry genes responsible for genetic transformation of the plant. See, for example, Kado, C. I., *Crit. Rev. Plant. Sci.* 10:1 (1991). Descriptions of *Agrobacterium* vector systems and methods for *Agrobacterium*-mediated gene transfer are provided by Gruber et al., supra, Miki et al., supra, and Moloney et al., *Plant Cell Reports* 8: 238 (1989). See also, U.S. Pat. No. 5,563,055, (Townsend and Thomas), issued Oct. 8, 1996.

B. Direct Gene Transfer

Several methods of plant transformation, collectively referred to as direct gene transfer, have been developed as an alternative to *Agrobacterium*-mediated transformation. A generally applicable method of plant transformation is microprojectile-mediated transformation wherein DNA is carried on the surface of microprojectiles measuring 1 to 4 µm. The expression vector is introduced into plant tissues with a biolistic device that accelerates the microprojectiles to speeds of 300 to 600 m/s which is sufficient to penetrate plant cell walls and membranes. Sanford et al., *Part. Sci. Technol.* 5: 27 (1987), Sanford, J. C., *Trends Biotech.* 6: 299 (1988), Klein et al., *Bio/Technology* 6: 559-563 (1988), Sanford, J. C., *Physiol Plant* 79: 206 (1990), Klein et al., *Biotechnology* 10: 268 (1992). See also U.S. Pat. No. 5,015,580 (Christou, et al), issued May 14, 1991; U.S. Pat. No. 5,322,783 (Tomes, et al.), issued Jun. 21, 1994.

Another method for physical delivery of DNA to plants is sonication of target cells. Zhang et al., *Bio/Technology* 9: 996 (1991). Alternatively, liposome or spheroplast fusion have been used to introduce expression vectors into plants. Deshayes et al., *EMBO J.,* 4: 2731 (1985), Christou et al., *Proc Natl. Acad. Sci. U.S.A.* 84: 3962 (1987). Direct uptake of DNA into protoplasts using CaCl2 precipitation, polyvinyl alcohol or poly-L-ornithine have also been reported. Hain et al., *Mol. Gen. Genet.* 199: 161 (1985) and Draper et al., *Plant Cell Physiol.* 23: 451 (1982). Electroporation of protoplasts and whole cells and tissues have also been described. Donn et al., In Abstracts of VIIth International Congress on Plant Cell and Tissue Culture IAPTC, A2-38, p 53 (1990); D'Halluin et al., *Plant Cell* 4: 1495-1505 (1992) and Spencer et al., *Plant Mol. Biol.* 24: 51-61 (1994).

Following transformation of soybean target tissues, expression of the above-described selectable marker genes allows for preferential selection of transformed cells, tissues and/or plants, using regeneration and selection methods now well known in the art.

It is often desirable to have the DNA sequence in homozygous state which may require more than one transformation event to create a parental line, requiring transformation with a first and second recombinant DNA molecule both of which encode the same gene product. It is further contemplated in some of the embodiments of the process of the invention that a plant cell be transformed with a recombinant DNA molecule containing at least two DNA sequences or be transformed with more than one recombinant DNA molecule. The DNA sequences or recombinant DNA molecules in such embodiments may be physically linked, by being in the same vector, or physically separate on different vectors. A cell may be simultaneously transformed with more than one vector provided that each vector has a unique selection marker gene. Alternatively, a cell may be transformed with more than one vector sequentially allowing an intermediate regeneration step after transformation with the first vector. Further, it may be possible to perform a sexual cross between individual plants or plant lines containing different DNA sequences or recombinant DNA molecules preferably the DNA sequences or the recombinant molecules are linked or located on the same chromosome, and then selecting from the progeny of the cross, plants containing both DNA sequences or recombinant DNA molecules.

Expression of recombinant DNA molecules containing the DNA sequences and promoters described herein in transformed plant cells may be monitored using Northern blot techniques and/or Southern blot techniques known to those of skill in the art.

The transformed cells may then be regenerated into a transgenic plant. The regenerated plants are transferred to standard soil conditions and cultivated in a conventional manner.

After the expression or inhibition cassette is stably incorporated into regenerated transgenic plants, it can be transferred to other plants by sexual crossing. Any of a number of standard breeding techniques can be used, depending upon the species to be crossed.

It may be useful to generate a number of individual transformed plants with any recombinant construct in order to recover plants free from any position effects. It may also be preferable to select plants that contain more than one copy of the introduced recombinant DNA molecule such that high levels of expression of the recombinant molecule are obtained.

As indicated above, it may be desirable to produce plant lines which are homozygous for a particular gene. In some species this is accomplished rather easily by the use of another culture or isolated microspore culture. This is especially true for the oil seed crop Brassica napus (Keller and Armstrong, Z. flanzenzucht 80:100-108, 1978). By using these techniques, it is possible to produce a haploid line that carries the inserted gene and then to double the chromosome number either spontaneously or by the use of colchicine. This gives rise to a plant that is homozygous for the inserted gene, which can be easily assayed for if the inserted gene carries with it a suitable selection marker gene for detection of plants carrying that gene. Alternatively, plants may be self-fertilized, leading to the production of a mixture of seed that consists of, in the simplest case, three types, homozygous (25%), heterozygous (50%) and null (25%) for the inserted gene. Although it is relatively easy to score null plants from those that contain the gene, it is possible in practice to score the homozygous from heterozygous plants by southern blot analysis in which careful attention is paid to the loading of exactly equivalent amounts of DNA from the mixed population, and scoring heterozygotes by the intensity of the signal from a probe specific for the inserted gene. It is advisable to verify the results of the southern blot analysis by allowing each independent transformant to self-fertilize, since additional evidence for homozygosity can be obtained by the simple fact that if the plant was homozygous for the inserted gene, all of the subsequent plants from the selfed seed will contain the gene, while if the plant was heterozygous for the gene, the generation grown from the selfed seed will contain null plants. Therefore, with simple selfing one can easily select homozygous plant lines that can also be confirmed by southern blot analysis.

Creation of homozygous parental lines makes possible the production of hybrid plants and seeds which will contain a modified protein component. Transgenic homozygous parental lines are maintained with each parent containing either the first or second recombinant DNA sequence operably linked to a promoter. Also incorporated in this scheme are the advantages of growing a hybrid crop, including the combining of more valuable traits and hybrid vigor.

The nucleotide constructs of the invention also encompass nucleotide constructs that may be employed in methods for altering or mutating a genomic nucleotide sequence in an organism, including, but not limited to, chimeric vectors, chimeric mutational vectors, chimeric repair vectors, mixed-duplex oligonucleotides, self-complementary chimeric oligonucleotides, and recombinogenic oligonucleobases. Such nucleotide constructs and methods of use, such as, for example, chimeraplasty, are known in the art. Chimeraplasty involves the use of such nucleotide constructs to introduce site-specific changes into the sequence of genomic DNA within an organism. See, U.S. Pat. Nos. 5,565,350; 5,731,181; 5,756,325; 5,760,012; 5,795,972; and 5,871,984; all of which are herein incorporated by reference. See also, WO 98/49350, WO 99/07865, WO 99/25821, and Beetham et al. (1999) Proc. Natl. Acad. Sci. USA 96:8774-8778; herein incorporated by reference.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims. Thus, many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims.

The following examples are offered by way of illustration and not by way of limitation.

Example 1

Identification of Proteins that Interact with the Phytophthora Resistance Soybean Protein Rps1-k-2

In the United States, the annual soybean yield loss suffered from the root and stem rot disease caused by Phytophthora sojae is valued at about 300 million dollars. Very little is known about the signal transduction process involved in the expression of Phytophthora resistance in soybean. In order to identify signal transduction factors for Phytophthora resistance, a yeast two-hybrid system was applied using various baits derived from the soybean Phytophthora resistance protein, Rps1-k-2. Thirteen candidate signaling factors, interacting with Rps1-k-2 in vivo in yeast and in vitro, were isolated. RNA interference (RNAi) experiments were conducted to determine the possible roles of the Rps1-k-2-interacting proteins (RIP) in Phytophthora resistance. RNAi-mediated silencing of four putative RIPs, RIP1, RIP4, RIP6 and RIP13 resulted in loss of resistance against P. sojae. RIP1, RIP4, RIP6 and RIP13 encode 26S proteasome AAA-ATPase subunit RPT5a, a receptor kinase, an expressed protein and a type II metacaspase, respectively. We further characterized RIP13. It was isolated using the N-terminal 144 amino acids of Rps1-k-2 carrying the coiled-coil (CC) domain as the bait. The RIP13 protein showed 60% identity to the recently characterized mcII-Pa, a type II metacaspase from Norway spruce. RIP13 is rapidly induced upon infection with an avirulent P sojae race. We have shown that RNAi-induced RIP13 silencing leading to Phytophthora susceptibility was associated with reduced steady state RIP13 transcript levels. This study implicates that RIP13 may be analogous to the mammalian effectors caspases, and Rps1-k-2 may act as an 'adapter protein' like Apaf-1 in initiating plant hypersensitive response-related cell death machinery.

Introduction

Plants survive a variety of pathogen invasions through a network of preformed and induced responses (Dangl and Jones, 2001; Hammond-Kosack and Jones, 1996). Plant disease resistance genes (R) are the key players in specific gene-for-gene responses. R gene products activate defense responses following the recognition of pathogen delivered avirulence (Avr) gene products (Dangl and Jones, 2001; Hammond-Kosack and Jones, 1996). Over 60 R genes have been cloned and characterized from various plant species (Hammond-Kosack and Parker, 2003; Martin et al., 2003). The cloned R genes conferring resistance to diverse pathogens share highly conserved structural domains/motifs. The majority of R genes encode proteins containing nucleotide binding sites (NB) and leucine-rich repeats (LRR) domains. This NB-LRR class can be further divided into two subfamilies based on their predicted N-terminal structures. One subfamily (CC-NB-LRR) carries a coiled-coil or leucine zipper domain at the N-terminal region (Pan et al., 2000). Members of the other subfamily (TIR-NB-LRR) contain an N-terminal TIR domain showing homology to a domain found in *Drosophila* Toll and mammalian interleukin-1 receptors (Hammond-Kosack and Jones, 1996; Whitham et al., 1994). Although a large number of R genes have been cloned, our knowledge of the molecular mechanisms of R-Avr proteins recognition and downstream activation remains poor. Therefore, it is of great importance to identify proteins that interact with R proteins and participate in R gene-mediated signaling process.

It was previously proposed that plant R protein and pathogen Avr protein interact directly. Despite the extensive efforts in validating this model, the available data imply that it is rather a rare case. Molecular evidence supporting this model has been obtained only from four plant-pathogen interactions (Deslandes et al., 2003; Dodds et al., 2006; Jia et al., 2000; Scofield et al., 1996; Tang et al., 1996). Accumulating data have indicated that multiple proteins participate in R gene-mediated disease resistance. Extensive studies have been focused on searching components that participate in R gene-mediated specific resistance. Most of the identified signaling components participate in multiple R genes mediated resistance. In *Arabidopsis*, NDR1 and EDS1 are required for CC-NB-LRR and TIR-NB-LRR R proteins, respectively (Aarts et al., 1998; Martin et al., 2003). RAR1 plays a conserved role in both types of NB-LRR R proteins (Azevedo et al., 2002; Liu et al., 2002a; Warren et al., 1999). RAR1 interacts with SGT1b, ortholog of an essential regulator SGT1 for cell cycle in yeast (Azevedo et al., 2002). Both SGT1 and the RAR1-SGT1 complex interact with a ubiquitin ligase complex, which indicate that they may be involved in disease resistance related protein degradation pathways (Azevedo et al., 2002; Liu et al., 2002a; Peart et al., 2002). Several recent studies have also found that RAR1 and SGT1 are associated with the molecular chaperon HSP90 (Hubert et al., 2003; Liu et al., 2004; Liu et al., 2003; Takahashi et al., 2003).

Among the signaling components identified, some are involved in specific R gene-mediated disease resistance. RIN4 was identified as a binding partner of the avirulence protein AvrB in *Arabidopsis* (Mackey et al., 2002). It is essential for RPM1- and RPS2-mediated resistances and it positively regulates the RPM1 function, while its elimination initiates the RPS2-dependent hypersensitive cell death. RIN4 appears to interact not only with AvrB but also RPM1, RPS2, AvrRpm1 and AvrRpt2 (Axtell and Staskawicz, 2003; Mackey et al., 2003; Mackey et al., 2002). PBS1 encodes a serine/threonine kinase and it is required for RPS5 function. The cleavage of PBS1 by the avirulence protein AvrPphB activates the RPS5-mediated resistance, and the cleavage of PBS is independent of RPS5 (Shao et al., 2003). Rcr3 is specifically required for Cf-2-mediated resistance in tomato, and it interacts with Avr2 directly (Dixon et al., 2000; Rooney et al., 2005).

The yeast two-hybrid system has been successful in isolating interactors of R proteins that participate in signal transduction pathway for plant disease resistance. Proteins that interact specifically with several R gene products have been recently isolated. A novel protein At-RSH was shown to interact with the NB-ARC domain of RPP5 (van der Biezen et al., 2000). Several RPM1 interacting proteins have been identified through yeast two-hybrid screening, such as RIN2, RIN3, RIN4 and RIN13 (Al-Daoude et al., 2005; Holt et al., 2002; Hubert et al., 2003; Kawasaki et al., 2005; Mackey et al., 2002). Recently, both protein phosphatase 5 (PP5) and HSP90 were found to interact with the tomato I-2 (de la Fuente van Bentem et al., 2005). We previously reported the isolation of the CC-NB-LRR type soybean Rps1-k gene (Gao et al., 2005). Rps1-k confers resistance to *P. sojae*. In this study, we employed Rps1-k-2 in a yeast two-hybrid system with the aim to identify putative signal transduction factors involved in the expression of *Phytophthora* resistance in soybean.

Results

Screening of a Soybean Prey cDNA Library

Figure 1:
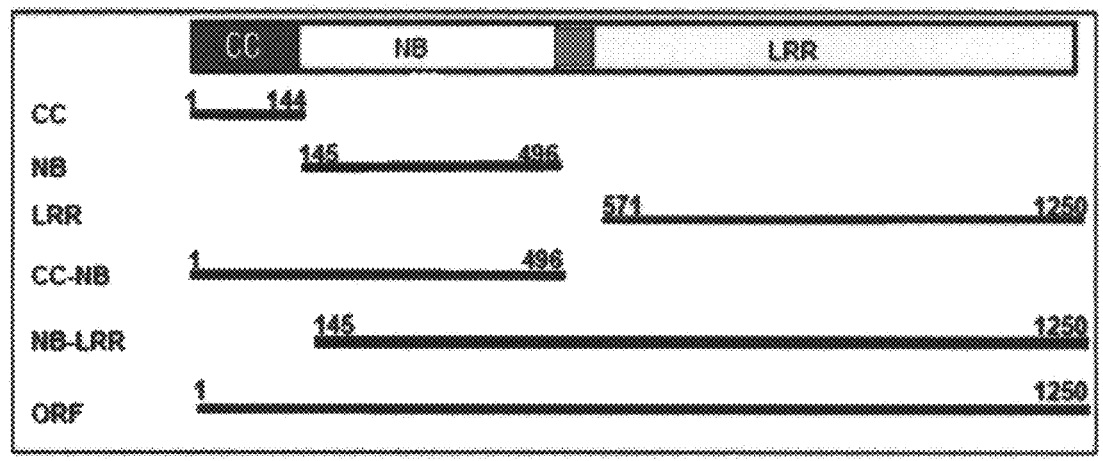
FIG. 1. Rps1-k-2 sequences used to develop bait plasmids in the pLexA vector. The structure of Rps1-k-2 is shown at the top. Domain and domain combinations used to develop baits (DBD-fusion plasmids) are shown with lines below the gene. The numbers above each line indicate the amino acid positions in Rps1-k-2. CC, Rps1-k-2-CC bait that contains the CC domain; NB, Rps1-k-2-NB bait that contains the nuclear-binding domain; LRR, Rps1-k-2-LRR bait that contains the LRR domain; CC-NB, Rps1-k-2-CC-NB bait that contains the CC and NB domains; NB-LRR, Rps1-k-2-NB-LRR bait that contains the NB and LRR domains; ORF, the full length Rps1-k-2 as bait.

To identify proteins that interact with Rps1-k-2, six bait proteins were generated by fusing individual domains, CC, NBS and LRR, as well as domain combinations, CC-NBS, NBS-LRR, and the Rps1-k-2 open reading frame (ORF), to the DNA-binding domain of the pLexA vector (FIG. 1). An unamplified prey cDNA library (>1.2×10⁶ colony forming units) was generated from the poly (A+) RNAs of the *P. sojae*-infected etiolated hypocyl tissues of the resistant cultivar, Willimas 82, harvested two and four hours following inoculation.

Figure 2:
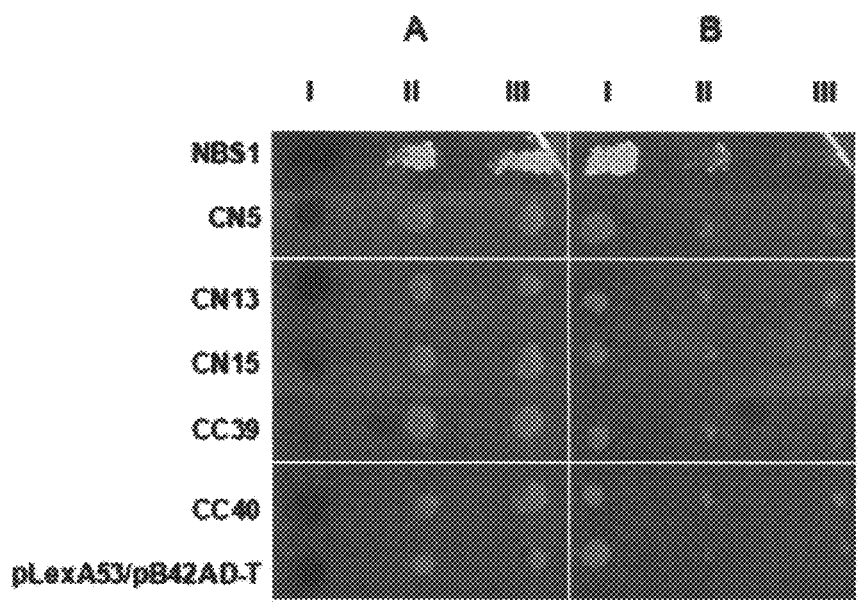
FIG. 2. In vivo interaction study between Rps1-k-2 and putative Rps1-k-2 interacting proteins. The indicated AD prey plasmids in yeast EGY48/pSH18-34 were recovered by random loss of DNA-BD bait plasmids. Colonies that grew on SD medium containing His but not on medium lacking His should have lost their DNA-BD plasmids, which were further confirmed by PCR with both pLexA primers (for DNA-BD plasmids) and pB42AD primers (for AD/library plasmids). The recovered AD prey plasmids in yeast EGY48/pSH18-34 were then re-transformed with the corresponding DNA-BD bait plasmids. A. Transformants grew on Gal/Raf/Xgal/CM-His-Trp-Ura plate. B. Transformants grew on Gal/Raf/CM-His-Trp-Ura-Leu plate. I. Candidate AD/library plasmids transformed with the corresponding DNA-BD bait plasmids; II. Candidate AD/library plasmids transformed with the empty bait vector pLexA; III. Candidate AD/library plasmids transformed with a nonspecific bait pLexA-Lam. A specific interaction was indicated by blue color of expression of the LacZ reporter gene, and by growth on minimum medium lacking Leucine from expression of the Leu2 reporter gene. NBS1 was isolated using the Rps1-k-NB bait; CN5, CN13 and CN15 were isolated using the Rps1-k-NB bait; CC39, CC40 were isolated using the Rps1-k-CC bait. pLexA-53, murine p53 (72-390 aa) in the pLexA vector; pB42AD-T, SV40 large T-antigen (87-708 aa) in the pB42AD vector; pLexA-Lam, DNA-BD-fused to human lamin C. pLexA-53 and pB42AD-T were used as positive control which interact strongly.

A total of 140 putative Rps1-k-2-interactors were identified from screening approximately 19.6 million yeast transformants (Table 1). The putative positive cDNA clones were sequenced. They were classified into 45 groups based on restriction mapping and sequencing data (Table 1). To eliminate some of the false positive clones, clones representing each group were then re-investigated for their in vivo interactions with the corresponding baits, the empty bait vector pLexA and a non-specific human Lamin C protein in yeast (FIG. 2). As shown in Table 1, 21 of the clones showed in vivo interactions with their respective bait proteins in the second screening. Some of the clones were isolated more than once or by more than one bait. For instance, the cDNA clone encoding a receptor kinase was isolated four times and displayed interaction with both the CC domain and NB-ARC domain of Rps1-k-2.

In Vitro Pull Down Assay

Figure 3:
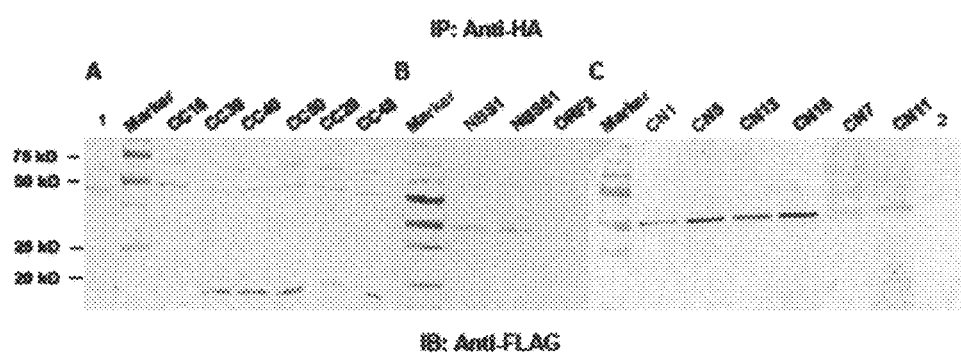
FIG. 3. In vitro interaction between Rps1-k-2 and Rps1-k-2-interactors. Putative positive Rps1-k-2 interactors were HA-tagged at their N-termini. All the baits were tagged at the N-termini with the FLAG epitope. Methodology for pull down assay was described in Materials and Methods.

In vitro interactions between the 21 putative Rps1-k-2-interactors and corresponding baits were next determined by conducting in vitro pull down assays. The DNA templates for in vitro protein synthesis were generated by PCR, and the PCR products were applied directly for protein synthesis. All the baits were fused to an N-terminal FLAG epitope. The putative Rps1-k-2-interactors were produced as hemaglutinin (HA)-tagged proteins. HA-tagged putative interactors were immobilized on anti-HA agarose. The immobilized proteins were subsequently incubated with their corresponding FLAG-tagged bait proteins. Binding proteins were eluted from anti-HA agarose loaded column followed by separation on SDS polyacrylamide gel. Specific interactions were examined by immunoblot analysis using Anti-FLAG M2 monoclonal antibody conjugated to alkaline phosphatase. As shown in FIG. 3, distinct bands corresponding to the predicted size of various baits were present in five clones for the CC bait, two clones for the NBS bait, and six clones for the bait of CC combined NBS. In contrast, no signals were observed where i) baits were expressed alone, ii) the expressed baits and the TNT translational reaction mix were used, and iii) eight of the 21 putative Rps1-k-2-interactors were mixed with their respective bait proteins. Therefore, 13 out of 21 interactors showed in vitro interactions with their corresponding baits. The 13 putative Rps1-k-2-interactors were termed as RIP1 (Rps1-k-2-interacting protein 1) through RIP13. They were annotated with the BLASTX algorithm (Table 2).

Silencing of Candidate Rps1-k-2-Interactors Through RNA Interference

To investigate the possible role of the Rps1-k-2-interactors in Rps1-k-2-mediated *Phytophthora* resistance, RNA interference (RNAi) was conducted. Recently, isoflavone synthase (IFS), a key enzyme for the formation of the isoflavones in soybean, has been successfully down regulated through RNAi in *Agrobacterium rhizogenes* transformed adventitious roots (Subramanian et al., 2005). We adapted and modified the RNAi procedure of Subramanian et al. (2005) for studying the function of the putative Rps1-k-2-interactors. A sequence segment of each putative Rps1-k-2-interactor gene was cloned in the pHANNIBAL vector in both sense and antisense orientations that are separated by the PDK intron (Wesley et al., 2001). Resulting vectors were sequenced to ensure that target sequences were indeed cloned as inverted repeat. The NotI fragments from the vector pHANNIBAL containing individual gene constructs for RNAi were then moved into the binary vector pART27:35 SGFP. Cotyledons of the resistant soybean cultivar Williams 82 were transformed with *A. rhizogenes* strain K599 carrying individual RNAi construct. Cotyledons of Willimas 82 and of the susceptible cultivar Williams, were also transformed with *A. rhizogenes* strain K599 carrying the empty vector used for developing RNAi constructs.

Not every hairy root developed following *A. rhizogenes* infection is transformed, therefore, to monitor successful transformation of hairy roots with the RNAi constructs or the empty vector, a 35S:GFP fusion reporter gene was cloned into the SacI site of the binary vector pART27 (Wesley et al., 2001). Expression of GFP was detected in the pART27:GFP transformed roots. There was however no GFP expression from the reporter gene in the transformed hairy roots when RNAi constructs of individual genes were incorporated into pART27:GFP. Presumably silencing of GFP was mediated by the 5'-end untranslated sequence specific to the 35S promoter fused to both RNAi-constructs and GFP. Without knowing which root was transformed with the RNAi constructs, it was impossible to evaluate the effect of gene silencing on the expression of *Phytophthora* resistance in the hairy roots. It has been reported that RNAi-induced gene silencing can be systemic (Voinnet, 2005). Systemic gene silencing mediated through RNAi has been reported in soybean (Subramanian et al., 2005). Therefore, four weeks after transformation with *A. rhizogenes* K599 carrying the empty vector or individual RNAi constructs, the cotyledons were inoculated with the *P. sojae* avirulent isolate 997A-2-3 at the *A. rhizogenes* K599 inoculation sites.

As shown in FIG. 4A, most of the Williams 82 cotyledons transformed with the empty vector remained resistant when *P. sojae* isolate 997A-2-3 was used to inoculate. Only about 17% of the cotyledons showed susceptibility (FIG. 4B). As expected, cotyledons of the susceptible cultivar, Williams, transformed with the empty vector displayed 100% susceptibility. The RIP11-RNAi construct for silencing the interactor RIP11, did not alter the resistant response of Williams 82. RNAi constructs developed for a few Rps1-k-2-interactor genes resulted in loss of Rps1-k-2-mediated resistance in majority of the Williams 82 cotyledons (FIG. 4B). These results suggest that the 26S proteasome AAA-ATPase subunit RPT5a encoded by RIP1, the putative receptor protein kinase encoded by RIP4 and RIP10, the unknown expressed protein encoded by RIP6, and a type II metacaspase encoded by RIP13 play essential roles in Rps1-k-2-mediated resistance.

RIP13 Encodes a Type II Metacaspase

Metacaspases are a family of distant relatives of caspases. They have been identified in plants, fungi and protozoa (Uren et al., 2000). Caspases are the executors of apoptosis in animals (Cohen, 1997). The possible role of metacaspase involved in plant-pathogen interaction has been implied from several studies. In *Arabidopsis*, all type I metacaspases and two type II metacaspases (AtMCP2b/Atmc5 and AtMCP2d/Atmc4) are rapidly induced upon infection with bacterial pathogens (Watanabe and Lam, 2005). The tomato type II metacapase LeMCA1 was found induced upon infection with *Botrytis cinerea* (Hoeberichts et al., 2003). A type II metacaspase from *Arabidopsis* was reported to regulate apoptosis in yeast (Madeo et al., 2002). A type II metacaspase, mcII-pa, from Norway spruce was recently found to execute PCD during plant embryogenesis (Bozhkov et al., 2005). All these findings imply that metacaspases may play a role in initiating cell death following pathogen infection. Hence, we further characterized RIP13, the Rps1-k-2-interactor that encodes a type II metacaspase.

To obtain the full-length cDNA sequence of RIP13, a gene-specific primer was designed to conduct 5'-rapid amplification of cDNA ends (RACE). Several independent clones were sequenced. A clone carrying the longest sequence and sharing complete sequence identity with the original clone was selected for further study. RIP13 has a coding region of 1275 bp and encodes a protein of 424 amino acids. Based on its sequence alignment with nine metacaspases from *Arabidopsis* and the recently characterized mcII-Pa from Norway spruce we conclude that RIP13 encodes a type II metacaspase (Bozhkov et al., 2005; Vercammen et al., 2004). As in mcII-Pa, the Arg residue at position 187 (R187) separates a p20 caspase-like subunit and a type II metacaspase-specific linker in RIP13. After the linker sequence a Lys residue (K271) separates the linker from the C-terminal p10 caspase-like subunit (FIG. 5). The sequence context of the catalytic histidine and cystein residues are conserved (Vercammen et al., 2004).

Reduced RIP13 Transcript Levels Following RNAi in Soybean Cotyledons.

To determine the extent to which RNAi reduced the steady state transcript levels of RIP13 in causing susceptibility, an RT-PCR approach was applied to the randomly selected cotyledons that were silenced for RIP13. As shown in FIG. 4, RNAi-mediated silencing of RIP13 resulted in loss of Rps1-k-2-mediated *Phytophthora* resistance in 65% of the Williams 82 cotyledons. In over 50% of the cotyledons transformed with the RNAi construct for RIP13, the steady state levels of RIP13 transcripts were reduced (FIG. 6).

RIP13 is Upregulated During Incompatible Soybean-Phytophthora Interaction

Induction of metacaspases transcripts has been observed in several studies (Sanmartin et al., 2005). To determine if RIP13 is induced following *P. sojae* infection, RT-PCR approach was applied to measure the steady state mRNA levels following infection of Williams 82 with an avirulent *P. sojae* race. RIP13 could be detected in uninfected tissues. One hour after *P. sojae* inoculation, the steady state RIP13 transcript level started to increase; at 2 h it reached the maximum. Thereafter, the RIP13 transcript level started to decrease (FIG. 7). This observation indicates that the expression of RIP13 is induced upon infection with the *P. sojae* avirulent isolate, 997A-2-3.

Discussion

Intra-molecular interaction has been reported from studies of two CC-NB-LRR-type R proteins, Mi-2 and Rx. The intramolecular interactions of Rx are lost during infection or elicitation, presumably to make the domains open for interaction with signaling factors (Hwang and Williamson, 2003; Moffett et al., 2002). These observations are supported by the recent finding that the TIR-NB-ARC region of the *Arabidopsis* TIR-NB-LRR R protein RPP1A alone induces constitutive immunity (Michael et al., 2006). In a yeast two-hybrid system, the intra-molecular interactions are most likely persistent due to the absence of the cognate ligands, and domains and/or motifs of R proteins necessary for interaction with signaling factors are unavailable. Therefore, individual domains and various domain combinations were generated from Rps1-k-2 and used as baits in a LexA-based yeast two-hybrid system for isolating Rps1-k-2-interactors.

Thirteen candidate Rps1-k-2-interacting proteins (RIPs) showing in vitro interaction with their respective baits were identified (Table 2). Based on sequence information of these proteins a few selected Rps1-k-2-interactors were further investigated for their possible functions. It is very unlikely that all 13 proteins interact in vivo with Rps1-k-2 and participate in signaling for disease resistance responses. Some of these factors such as 2'-hydroxydihydrodaidzein reductase and starch branching enzyme are unusual. They most likely came through as artifacts. Alternatively, these are true Rps1-k-2-interactors. 2'-hydroxydihydrodaidzein reductase is involved in phytoalexin synthesis in elicitor-challenged soybean (Fischer et al., 1990). It may be possible that 2'-hydroxydihydrodaidzein reductase negatively regulates Rps1-k-2 and suppresses its function once the enzyme is accumulated sufficiently for phytoalexin production. Similarly, down-regulation of starch metabolism by Rps1-k-2 could also be possible in order to utilize the available resources for producing defense compounds including phytoalexins. It has been previously reported that in infected soybean cell suspensions the levels of inositol tris-phosphate (IP3), a second messenger for growth and DNA replication, are reduced presumably to facilitate phytoalexin biosynthesis (Shigaki and Bhattacharyya, 2000, 2002).

Both our FRET and RNAi data suggested that the identified Rps1-2-interactors, RIP1 encoding an AAA ATPase/26S proteasome subunit, RIP13 encoding a Type II metacaspase, RIP6 encoding an expressed protein, and RIP4 and RIP10 encoding putative kinase receptors are the most promising Rps1-k-2-interactors. The 26S proteosome is composed of a 19S regulatory particle and a 20S catalytic complex, with each complex composed of several subunits. The regulatory complex controls the access of substrates to the catalytic complex containing the protease activities (Sullivan et al., 2003; Vierstra, 2003).

Recent data have suggested that the ubiquitin/26S proteasome pathway plays a major role in regulating protein stability including plant disease resistance proteins (Vierstra, 2003). COP9 signalosome, another multiple protein complex, can associate with the 26S proteasome as well as several E3-ligase complexes. Liu et al. (2002b) found that silencing of the COP9 signalosome can compromise N-mediated resistance to TMV in *Nicotiana benthanianum*. It was recently reported that the AvrPtoB type III effector utilizes host E3 ubiquitin ligase activity to suppress plant cell death and immunity in tomato (Abramovitch et al., 2006).

RIP6 encodes a novel protein. It is unusual in that it has a stretch of nine asparagines (N). Two types of full length ESTs were found when using RIP6 as query sequence against the soybean EST database. Most of the ESTs encoding identical or near identical protein as RIP6 are from salicylic acid induced or pathogen-challenged tissues. As shown in FIG. 8, these homologs have various numbers of trinucleotide repeat sequence (encode asparagines). Protein segments containing high number of glutamines (Q) and/or asparagines (N) are called prion domains (Sherman, 2004). PolyQ or polyN sequences are often found in transcription factors and protein kinases. Little is known about the function of these Q/N-rich domains (Sherman, 2004). This expressed protein RIP6 appears to play an important role in Rps1-k encoded resistance based on our preliminary RNAi data. It will be interesting to investigate if the gene represents a polymorphic microsatellite sequence among soybean lines in addition to learning the mechanism by which it participate in the expression of *Phytophthora* resistance.

Four clones obtained in the initial yeast two-hybrid screens encode putative receptor protein kinase. Three identical clones including RIP4 were isolated by using the Rps1-k-2 CC-NB bait, and the fourth one RIP10 by using the Rps1-k-2 CC bait. The deduced proteins of RIP4 and RIP10 share high sequence identity. They all carry the C-terminal region of the tyrosine kinase domain. Silencing of RIP4 and RIP10 resulted in loss of *Phytophthora* resistance (FIG. 4). The importance of kinase in plant immunity and disease resistance has been demonstrated. Some disease resistance genes such as Pto, Xa21 and Rpg1 encode kinases. Many mitogen-activated protein kinases (MAPK) have shown essential roles in plant disease resistance. A complete MAP kinase cascade activated in response to elicitor, flagellin, has been characterized (Asai et al., 2002). A Ser/Thr protein kinase ACIK1 is found essential for complete Cf-9 dependent disease resistance in tomato (Rowland et al., 2005). It is possible that Rps1-k-2 interacts with RIP4 following infection and activates the kinase for regulating downstream signaling proteins.

Metacaspases in plants are classified as type I and type II. Several studies have implicated a possible role of metacaspases in the activation of cell death. Here we demonstrated the interaction between RIP13, a type II metacaspase, with the N-terminal 144 amino acids carrying the coiled-coil (CC) domain of Rps1-k-2. Silencing of RIP13 resulted in loss of Rps1-k-2-mediated *Phytophthora* resistance. It is not known whether type II metacaspases interact with other plant R gene products. The majority of R gene products share not only a NB-ARC domain but also a structural similarity to Apaf-1/CED-4 that are involved in apoptosis (Van der Biezen and Jones, 1998). A clear model for the function of Apaf-1/CED-4 has been established. Upon an apoptotic stimulus, cytocrome c is released from mitochondria into cytosol and binds to Apaf-1. In the presence of dATP, Apaf-1 oligomerized via a mutual interaction of the NB-ARC regions. Oligomerized Apaf-1 then recruits and activates procaspase 9, which in turn recruits and activates caspases 3, 6, 7 and engages a cascade of proteolytic events (Campioni et al., 2005)). Are the R gene products and Apaf-1/CED-4 functionally analogous? Apaf-1 interacts directly with procaspase 9 via their CARD domains. Caspase 3, which lacks a prodomain, does not interact directly with Apaf-1 (Li et al., 1997). In our study, we have shown the interaction between the N-terminal region of Rps1- k-2 with the C-terminus of the type II metacapase that does not possess any prodomain. The interacting C-terminal region of the protein contains 290 amino acids including 53 residues from the p-20 like domain, the linker sequence and the p-10 like domain (FIG. 5). The interaction between RIP13 and the CC domain of Rps1-k-2 is different from the one observed between Apaf-1 and procaspase 9 that interact through their CARD domains. Plant R gene products may act as 'adaptor protein' like Apaf-1 to recruit components like metacaspases in plant hypersensitive response (HR) related cell death machinery (Van der Biezen and Jones, 1998).

In summary, use various domains of soybean disease resistance protein Rps1-k-2 in a yeast two-hybrid system allowed cloning four signaling genes for *Phytophthora* resistance in soybean. RNAi-induced silencing of the genes encoding these factors suggested that these are essential for *Phytophthora* resistance. This suggest that Rps1-k-2-mediated *Phytophthora* resistance in soybean is mediated through interaction of the disease resistance protein with multiple factors, and is not unusual considering the complexity of disease resistance signaling pathway observed in other plant-pathogen interaction.

Materials and Methods

Yeast 2-Hybrid System

LexA-based yeast two-hybrid system was performed in this study. All bait constructs including the full-length Rps1-k-2, CC domain, NBS domain, LRR domain, CC and NB domains, NB and LRR domains were PCR amplified and cloned into the BamHI-XhoI sites of the bait vector pLexA (Clontech Laboratories, Inc., Mountain View, Calif.) (All the primers used are presented in Table 3). A yeast two-hybrid cDNA library was constructed with the pBluescript II XR cDNA library construction kit (Stratagene, La Jolla, Calif.). Briefly, total RNA was prepared from infected etiolated Williams 82 hypocotyl tissues harvested 2 and 4 hours following *P. sojae* inoculation. poly(A+) RNA was extracted using the poly(A)tract mRNA isolation system III (Promega, Madison Wis.). The ready EcoRI/XhoI cut cNDAs were cloned into the EcoRI/XhoI sites of the vector pB42AD.

Yeast two-hybrid screen was performed in the yeast strain EGY48 (Clontech, Mountain View, Calif.) with two reporter genes LEU2 and LacZ (Clontech, Mountain View, Calif.). Individual bait was first transformed into EGY48/pSH18-34. Auto-activation assay, repression assay and Leu requirement test were followed to test the suitability of the bait for yeast two-hybrid screen. The prey cDNA library was then screened with individual baits. Double transformants were selected for further characterization based on growth on synthetic medium (SD) lacking leucine, tryptophan, histidine and uracil, and development of a substantial blue color change as an indication of the expression of the LacZ reporter gene when grown on 5-bromo-4-chloro-3-indolyl-β-D-galactopyranoside (X-gal) plates lacking tryptophan, histidine and uracil. AD prey plasmids in yeast EGY48/pSH18-34 were recovered by random loss of DNA-BD bait plasmids. Individual DNA-BD bait plasmid was then retransformed into yeast EGY48/pSH18-34 with the corresponding AD prey plasmids retained. False positives were subsequently eliminated based on the interactions of individual prey with two negative control baits including the empty bait vector pLexA and a nonspecific bait pLexA-Lam (human lamin C (66-230) in pLexA) (Clontech, Mountain View, Calif.). Positive clones were sequenced with pB42AD specific primer (5'-CCAGC-CTCTTGCTGAGTGGAGATG-3'). Each sequence was queried with the GenBank/EMBL/DDBJ databases using the BLASTX algorithm (www.ncbi.nlm.nih.gov/BLAST).

In Vitro Pull-Down Assay

DNA templates for in vitro protein synthesis were generated by PCR (primers used are presented in Table 4). To enable efficient translation, a T7 promoter and the kozak consensus sequences were added to the 5'-end and a poly(A) 30 tail to the 3'-end of each target template. Both HA-tagged preys and FLAG-tagged baits were expressed using TNT® T7 quick for PCR system (Promega, Madison, Wis.). The TNT® reaction was performed as recommended by the manufacturer (Promega, Madison, Wis.). Twenty microliters of the TNT® reaction containing individual HA-tagged prey protein and six microliters anti-HA agrose slurry (Pierce Technology Corporation, Holmdel, N.J.) were added to a Handee™ Mini-Spin Column (Pierce Technology Corporation, Holmdel, N.J.) and incubated with gentle end-over-end mixing for two hours at 4° C. The column was washed three times with 500 µl of TBS-T (25 mM mM Tris.HCl [pH 7.2] and 0.15 M NaCl with 0.05% Tween®-20) and the anti-HA agarose was resuspended with 185 µl TBS. Fifteen microliters of the TNT® reaction containing the expressed bait proteins were added to the prepared anti-HA agarose carrying the respective immobilized prey proteins and incubated for two hours at room temperature. The column was washed four times in the same washing buffer used in the immobilization. 25 µl non-reducing sample buffer (Pierce Technology Corporation, Holmdel, N.J.) was added to the column and the column was heated at 95° C. for 5 minutes. The eluted samples were loaded onto a 12% Tris-glycine gel. The gel was transferred to a PVDF membrane. The membrane was then blocked with TBS-T/1% BSA for one hour at room temperature followed by two washing with TBS-T. Anti-FLAG M2 monoclonal antibody conjugated with alkaline phosphatase diluted to 1:1000 (Sigma, St. Louis, Mo.) in TBS-T was added to the membrane and incubated for 1 hour at room temperature. The membrane was washed six times in TBS-T. Bands were visualized using Western Blue® stabilized substrate for alkaline phosphatase (Promega, Madison, Wis.).

Generation of RNAi Vectors

All the RNAi constructs used to silence the putative Rps1-k-2-interactors were generated in a similar way. A fragment for each putative Rps1-k-2-interactors was amplified by PCR from the corresponding cDNA clones. Two primers were designed for each cDNA clone and each primer was tailed by two sets of proper restriction enzyme sites at the 5' end (Table 5). The PCR products were cloned in the pHANNIBAL vector as inverted repeat that are separated by a PDK (pyruvate orthophosphate dikinase) intron sequence (Wesley et al., 2001). The NotI fragments from pHANNIBAL containing ihp-cDNAs were then subcloned into the binary vector pART27:GFP. The pART27:GFP vector was obtained by cloning the 35S:GFP from p35S-GFP (Clontech, Mountain View, Calif.) into the Sac I site of pART27 (Wesley et al., 2001). Each RNAi construct was sequenced to confirm the correct orientation as inverted repeat.

Plant Materials

Soybean seedlings of Williams and Williams 82 were grown in coarse vermiculite in a Conviron Growth Chamber (22° C., 12 hour photoperiod) in the Agronomy Hall at Iowa State University. Seedlings were watered once on day 3. On day 7 cotyledons were harvested for *A. rhizogenes*-mediated transformation.

*Agrobacterium rhizogenes* Manipulation

The *A. rhizogenes* strain K599 was kindly provided by Dr. Thomas Baum, Iowa State University. Empty vector pART27GFP and the vector pART27GFP harboring individual RNAi constructs were transformed into the *A. rhizogenes* strain K599 by the freeze-thaw transformation method (An et al., 1988). Each RNAi construct and the empty vector in *A. rhizogenes* were grown in 10 ml LB at 28° C. with shaking at 250 rpm for two days. Before inoculation of the wounded cotyledons, the cultures were pelleted and the cells were resuspended in 10 mM MgSO4 (OD600=~0.3) (Subramanian, 2005).

*A. rhizogenes*-mediated transformation of soybean cotyledons

A protocol of soybean cotyledon transformation with *A. rhizogenes* described by Subramanian et al. (2005) was performed with modifications. Individual cotyledon was first surface sterilized with North O/H Pak alcohol wipes (North Safety Products, Cranston, R.I.). The centers of the surface-sterilized cotyledons were wounded with a 200 µl pipette tip. The wounded cotyledons were then placed on petri plates containing sterile Whatman filter papers (9 cm in diameter) moistened with 3.0 ml sterile ddH2O. Twenty microliter *A. rhizogenes* suspension in 10 mM MgSO4 was added into the circular holes made in individual cotyledons. Plates were then wrapped with Parafilm and cultured at 22° C. with a 12-h light cycle of ~150 µEs light intensity.

Infection of *A. rhizogenes* Transformed Cotyledons with *P. sojae*

*P. sojae* isolate 997A-2-3 was grown on lima bean agar plate in the dark at 22° C. Seven-day old *P. sojae* was used for infection. Four weeks after transformation of cotyledons with *A. rhizogenes* K599 carrying either the empty vector or individual RNAi constructs, a small piece (~2 mm×2 mm) of lima bean agar containing *P. sojae* mycellia was placed on the site of transformation. Seventy-two hours after *P. sojae* infection, the number of susceptible and resistance cotyledons were recorded and pictures were taken.

REFERENCES

Aarts, N., Metz, M., Holub, E., Staskawicz, B. J., Daniels, M. J., and Parker, J. E. (1998) Different requirements for EDS1 and NDR1 by disease resistance genes define at least two R gene-mediated signaling pathways in *Arabidopsis*. Proc. Natl. Acad. Sci. USA 95, 10306-10311.

Abramovitch, R. B., Janjusevic, R., Stebbins, C. E., and Martin, G. B. (2006) Type III effector AvrPtoB requires intrinsic E3 ubiquitin ligase activity to suppress plant cell death and immunity. Proc. Natl. Acad. Sci. USA 103, 2851-2856.

Al-Daoude, A., de Torres Zabala, M., Ko, J. H., and Grant, M. (2005) RIN13 is a positive regulator of the plant disease resistance protein RPM1. Plant Cell 17, 1016-1028.

An, G., Ebert, P. R., Mitra, A., and Ha, S. B. (1988). Binary vectors. In Plant Molecular Biology Manual (Dordrecht: Kluwer Academic Publishers), pp. 1-19.

Asai, T., Tena, G., Plotnikova, J., Willmann, M. R., Chiu, W. L., Gomez-Gomez, L., Boller, T., Ausubel, F. M., and Sheen, J. (2002) MAP kinase signalling cascade in *Arabidopsis* innate immunity. Nature 415, 977-983.

Axtell, M. J., and Staskawicz, B. J. (2003) Initiation of RPS2-specified disease resistance in *Arabidopsis* is coupled to the AvrRpt2-directed elimination of RIN4. Cell 112, 369-377.

Azevedo, C., Sadanandom, A., Kitagawa, K., Freialdenhoven, A., Shirasu, K., and Schulze-Lefert, P. (2002) The RAR1 interactor SGT1, an essential component of R gene-triggered disease resistance. Science 295, 2073-2076.

Bozhkov, P. V., Suarez, M. F., Filonova, L. H., Daniel, G., Zamyatnin, A. A., Jr., Rodriguez-Nieto, S., Zhivotovsky, B., and Smertenko, A. (2005) Cysteine protease mcII-Pa executes programmed cell death during plant embryogenesis. Proc. Natl. Acad. Sci. USA 102, 14463-14468.

Campioni, M., Santini, D., Tonini, G., Murace, R., Dragonetti, E., Spugnini, E. P., and Baldi, A. (2005) Role of Apaf-1, a key regulator of apoptosis, in melanoma progression and chemoresistance. Exp. Dermatol. 14, 811-818.

Cohen, G. M. (1997) Caspases: the executioners of apoptosis. Biochem. J. 326, 1-16.

Dangl, J. L., and Jones, J. D. (2001) Plant pathogens and integrated defense responses to infection. Nature 411, 826-833.

de la Fuente van Bentem, S., Vossen, J. H., de Vries, K. J., van Wees, S., Tameling, W. I., Dekker, H. L., de Koster, C. G., Haring, M. A., Takken, F. L., and Cornelissen, B. J. (2005) Heat shock protein 90 and its co-chaperone protein phosphatase 5 interact with distinct regions of the tomato 1-2 disease resistance protein. Plant J. 43, 284-298.

Deslandes, L., Olivier, J., Peeters, N., Feng, D. X., Khounlotham, M., Boucher, C., Somssich, I., Genin, S., and Marco, Y. (2003) Physical interaction between RRS1-R, a protein conferring resistance to bacterial wilt, and PopP2, a type III effector targeted to the plant nucleus. Proc. Natl. Acad. Sci. USA 100, 8024-8029.

Dixon, M. S., Golstein, C., Thomas, C. M., van Der Biezen, E. A., and Jones, J. D. (2000) Genetic complexity of pathogen perception by plants: the example of Rcr3, a tomato gene required specifically by Cf-2. Proc. Natl. Acad. Sci. USA 97, 8807-8814.

Dodds, P. N., Lawrence, G. J., Catanzariti, A. M., Teh, T., Wang, C. I., Ayliffe, M. A., Kobe, B., and Ellis, J. G. (2006) Direct protein interaction underlies gene-for-gene specificity and coevolution of the flax resistance genes and flax rust avirulence genes. Proc. Natl. Acad. Sci. USA 103, 8888-8893.

Fischer, D., Ebenau-Jehle, C., and Grisebach, H. (1990) Phytoalexin synthesis in soybean: purification and characterization of NADPH:2'-hydroxydaidzein oxidoreductase from elicitor-challenged soybean cell cultures. Arch. Biochem. Biophys. 276, 390-395.

Gao, H., Narayanan, N. N., Ellison, L., and Bhattacharyya, M. K. (2005) Two classes of highly similar coiled coil-nucleotide binding-leucine rich repeat genes isolated from the Rps1-k locus encode *Phytophthora* resistance in soybean. Mol. Plant. Microbe Interact. 18, 1035-1045.

Hammond-Kosack, K. E., and Jones, J. D. G. (1996) Resistance gene-dependent plant defense responses. Plant Cell 8, 1773-1791. 158

Hammond-Kosack, K. E., and Parker, J. E. (2003) Deciphering plant-pathogen communication: fresh perspectives for molecular resistance breeding. Curr. Opin. Biotechnol. 14, 177-193.

Hoeberichts, F. A., ten Have, A., and Woltering, E. J. (2003) A tomato metacaspase gene is upregulated during programmed cell death in *Botrytis cinerea*-infected leaves. Planta 217, 517-522.

Holt, B. F., 3rd, Boyes, D. C., Ellerstrom, M., Siefers, N., Wiig, A., Kauffman, S., Grant, M. R., and Dangl, J. L. (2002) An evolutionarily conserved mediator of plant disease resistance gene function is required for normal *Arabidopsis* development. Dev. Cell 2, 807-817.

Hubert, D. A., Tornero, P., Belkhadir, Y., Krishna, P., Takahashi, A., Shirasu, K., and Dangl, J. L. (2003) Cytosolic HSP90 associates with and modulates the *Arabidopsis* RPM1 disease resistance protein. EMBO J. 22, 5679-5689.

Hwang, C. F., and Williamson, V. M. (2003) Leucine-rich repeat-mediated intramolecular interactions in nematode recognition and cell death signaling by the tomato resistance protein Mi. Plant J. 34, 585-593.

Jia, Y., McAdams, S. A., Bryan, G. T., Hershey, H. P., and Valent, B. (2000) Direct interaction of resistance gene and avirulence gene products confers rice blast resistance. EMBO J. 19, 4004-4014.

Kawasaki, T., Nam, J., Boyes, D. C., Holt, B. F., 3rd, Hubert, D. A., Wiig, A., and Dangl, J. L. (2005) A duplicated pair of Arabidopsis RING-finger E3 ligases contribute to the RPM1- and RPS2-mediated hypersensitive response. Plant J. 44, 258-270.

Li, P., Nijhawan, D., Budihardjo, I., Srinivasula, S. M., Ahmad, M., Alnemri, E. S., and Wang, X. (1997) Cytochrome c and dATP-dependent formation of Apaf-1/caspase-9 complex initiates an apoptotic protease cascade. Cell 91, 479-489.

Liu, Y., Schiff, M., Marathe, R., and Dinesh-Kumar, S. P. (2002a) Tobacco Rar1, EDS1 and NPR1/NIM1 like genes are required for N-mediated resistance to tobacco mosaic virus. Plant J. 30, 415-429.

Liu, Y., Schiff, M., Serino, G., Deng, X. W., and Dinesh-Kumar, S. P. (2002b) Role of SCF ubiquitin-ligase and the COP9 signalosome in the N gene-mediated resistance response to tobacco mosaic virus. Plant Cell 14, 1483-1496.

Liu, Y., Burch-Smith, T., Schiff, M., Feng, S., and Dinesh-Kumar, S. P. (2004) Molecular chaperone Hsp90 associates with resistance protein N and its signaling proteins SGT1 and Rar1 to modulate an innate immune response in plants. J. Biol. Chem. 279, 2101-2108.

Liu, Y., Jin, H., Yang, K. Y., Kim, C. Y., Baker, B., and Zhang, S. (2003) Interaction between two mitogen-activated protein kinases during tobacco defense signaling. Plant J. 34, 149-160.

Mackey, D., Holt, B. F., Wiig, A., and Dangl, J. L. (2002) RIN4 interacts with Pseudomonas syringae type III effector molecules and is required for RPM1-mediated resistance in Arabidopsis. Cell 108, 743-754.

Mackey, D., Belkhadir, Y., Alonso, J. M., Ecker, J. R., and Dangl, J. L. (2003) Arabidopsis RIN4 is a target of the type III virulence effector AvrRpt2 and modulates RPS2-mediated resistance. Cell 112, 379-389.

Madeo, F., Herker, E., Maldener, C., Wissing, S., Lachelt, S., Herlan, M., Fehr, M., Lauber, K., Sigrist, S. J., Wesselborg, S., and Frohlich, K. U. (2002) A caspase-related protease regulates apoptosis in yeast. Mol. Cell. 9, 911-917.

Martin, G. B., Bogdanove, A. J., and Sessa, G. (2003) Understanding the functions of plant disease resistance proteins. Annu. Rev. Plant Biol. 54, 23-61.

Michael, W. L., Swiderski, M. R., Li, Y., and Jones, J. D. (2006) The Arabidopsis thaliana TIR-NB-LRR R-protein, RPP1A; protein localization and constitutive activation of defense by truncated alleles in tobacco and Arabidopsis. Plant J. 47, 829-840.

Moffett, P., Farnham, G., Peart, J., and Baulcombe, D. C. (2002) Interaction between domains of a plant NBS-LRR protein in disease resistance-related cell death. EMBO J. 21, 4511-4519.

Pan, Q., Wendel, J., and Fluhr, R. (2000) Divergent evolution of plant NBS-LRR resistance gene homologues in dicot and cereal genomes. J. Mol. Evol. 50, 203-213.

Peart, J. R., Cook, G., Feys, B. J., Parker, J. E., and Baulcombe, D. C. (2002) An EDS1 orthologue is required for N-mediated resistance against tobacco mosaic virus. Plant J. 29, 569-579.

Rooney, H. C., Van't Klooster, J. W., van der Hoorn, R. A., Joosten, M. H., Jones, J. D., and de Wit, P. J. (2005) Cladosporium Avr2 inhibits tomato Rcr3 protease required for Cf-2-dependent disease resistance. Science 308, 1783-1786.

Rowland, O., Ludwig, A. A., Merrick, C. J., Baillieul, F., Tracy, F. E., Durrant, W. E., Fritz-Laylin, L., Nekrasov, V., Sjolander, K., Yoshioka, H., and Jones, J. D. (2005) Functional analysis of Avr9/Cf-9 rapidly elicited genes identifies a protein kinase, ACIK1, that is essential for full Cf-9-dependent disease resistance in tomato. Plant Cell 17, 295-310.

Sanmartin, M., Jaroszewski, L., Raikhel, N. V., and Rojo, E. (2005) Caspases. Regulating death since the origin of life. Plant Physiol. 137, 841-847.

Scofield, S. R., Tobias, C. M., Rathjen, J. P., Chang, J. H., Lavelle, D. T., Michelmore, R. W., and Staskawicz, B. J. (1996) Molecular basis of gene-for-gene specificity in bacterial speck disease of tomato. Science 274, 2063-2065.

Shao, F., Golstein, C., Ade, J., Stoutemyer, M., Dixon, J. E., and Innes, R. W. (2003) Cleavage of Arabidopsis PBS1 by a bacterial type III effector. Science 301, 1230-1233.

Sherman, M. Y. (2004) Yeast prions: protein aggregation is not enough. PLoS Biol. 2, E125.

Shigaki, T., and Bhattacharyya, M. K. (2000) Decreased inositol 1,4,5-trisphosphate content in pathogen-challenged soybean cells. Mol. Plant. Microbe Interact. 13, 563-567.

Shigaki, T., and Bhattacharyya, M. K. (2002) Nutrient induced an increase in inositol 1,4,5-trisphosphate in soybean cells: implication for the involvement of phosphoinositide-specific phospholipase C in DNA synthesis. Plant Biol. 4, 53-61.

Subramanian, S., Graham, M. Y., Yu, O., and Graham, T. L. (2005) RNA interference of soybean isoflavone synthase genes leads to silencing in tissues distal to the transformation site and to enhanced susceptibility to Phytophthora sojae. Plant Physiol. 137, 1345-1353.

Sullivan, J. A., Shirasu, K., and Deng, X. W. (2003) The diverse roles of ubiquitin and the 26S proteasome in the life of plants. Nat. Rev. Genet. 4, 948-958.

Takahashi, A., Casais, C., Ichimura, K., and Shirasu, K. (2003) HSP90 interacts with RAR1 and SGT1 and is essential for RPS2-mediated disease resistance in Arabidopsis. Proc. Natl. Acad. Sci. USA 100, 11777-11782.

Tang, X., Frederick, R. D., Zhou, J., Halterman, D. A., Jia, Y., and Martin, G. B. (1996) Initiation of plant disease resistance by physical interaction of AvrPto and Pto kinase. Science 274, 2060-2063.

Uren, A. G., O'Rourke, K., Aravind, L. A., Pisabarro, M. T., Seshagiri, S., Koonin, E. V., and Dixit, V. M. (2000) Identification of paracaspases and metacaspases: two ancient families of caspase-like proteins, one of which plays a key role in MALT lymphoma. Mol. Cell. 6, 961-967.

Van der Biezen, E. A., and Jones, J. D. (1998) Plant disease-resistance proteins and the gene-for-gene concept. Trends Biochem. Sci. 23, 454-456.

van der Biezen, E. A., Sun, J., Coleman, M. J., Bibb, M. J., and Jones, J. D. (2000) Arabidopsis RelA/SpoT homologs implicate (p)ppGpp in plant signaling. Proc. Natl. Acad. Sci. USA 97, 3747-3752.

Vercammen, D., van de Cotte, B., De Jaeger, G., Eeckhout, D., Casteels, P., Vandepoele, K., Vandenberghe, I., Van Beeumen, J., Inze, D., and Van Breusegem, F. (2004) Type II metacaspases Atmc4 and Atmc9 of Arabidopsis thaliana cleave substrates after arginine and lysine. J. Biol. Chem. 279, 45329-45336.

Vierstra, R. D. (2003) The ubiquitin/26S proteasome pathway, the complex last chapter in the life of many plant proteins. Trends Plant Sci. 8, 135-142.

Voinnet, O. (2005) Non-cell autonomous RNA silencing. FEBS Lett. 579, 5858-5871.

Warren, R. F., Merritt, P. M., Holub, E., and Innes, R. W. (1999) Identification of three putative signal transduction genes involved in R gene-specified disease resistance in Arabidopsis. Genetics 152, 401-412.

Watanabe, N., and Lam, E. (2005) Two *Arabidopsis* metacaspases AtMCP1b and AtMCP2b are arginine/lysine-specific cysteine proteases and activate apoptosis-like cell death in yeast. J. Biol. Chem. 280, 14691-14699.

Wesley, S. V., Helliwell, C. A., Smith, N. A., Wang, M. B., Rouse, D. T., Liu, Q., Gooding, P. S., Singh, S. P., Abbott, D., Stoutjesdijk, P. A., Robinson, S. P., Gleave, A. P., Green, A. G., and Waterhouse, P. M. (2001) Construct design for efficient, effective and high-throughput gene silencing in plants. Plant J. 27, 581-590.

Whitham, S., Dinesh-Kumar, S. P., Choi, D., Hehl, R., Corr, C., and Baker, B. (1994) The product of the tobacco mosaic virus resistance gene N: Similarity to toll and the interleukin-1 receptor. Cell 78, 1101-1115.

All references cited herein are hereby incorporated in their entirety by reference.

TABLE 1

Identification of putative Rps1-k-2-interactors from yeast two-hybrid screens of a soybean prey cDNA library

| DBD-fusion bait plasmid | Transformants screened (cfu)[1] | Putative interactors 1st Screen[2] | | 2nd Screen[3] |
|---|---|---|---|---|
| | | Clones | Classes | |
| pLexA_CC[4] | 7 × 10$^6$ | 44 | 17 | 12 |
| pLexA_NB | 4 × 10$^6$ | 71 | 16 | 2 |
| pLexA_LRR | 3 × 10$^5$ | 0 | 0 | 0 |
| pLexA_CC-NB | 6 × 10$^6$ | 16 | 6 | 6 |

TABLE 1-continued

Identification of putative Rps1-k-2-interactors from yeast two-hybrid screens of a soybean prey cDNA library

| DBD-fusion bait plasmid | Transformants screened (cfu)[1] | Putative interactors 1st Screen[2] | | 2nd Screen[3] |
|---|---|---|---|---|
| | | Clones | Classes | |
| pLexA_NB-LRR | 3 × 10$^5$ | 5 | 5 | 0 |
| pLexA_ORF | 2 × 10$^6$ | 4 | 1 | 1 |
| Total | 19.6 × 10$^6$ | 140 | 21 | 21 |

[1]Transformants containing both bait and prey plasmids.
[2]Clones identified following initial screen after transformation of the yeast strain containing bait plasmids with the prey cDNA library.
[3]Rescreening in yeast as shown in FIG. 2.
[4]The DBD-fusion bait plasmids were named as follows: each one starts with the bait vector pLexA followed by the name of different domains or domain combinations of Rps1-k-2.

TABLE 2

Candidate Rps1-k-2-interactors showing in vitro interaction with Rps1-k-2

| Clone ID[1] | Putative Annotation | E values |
|---|---|---|
| NBS1 | 26S proteasome AAA-Atpase subunit RPT5a | 3e−60 |
| NBS51 | 2'-hydroxydihydrodaidzein reductase | 2e−57 |
| CN1 | Putative ripening-related protein | 6e−04 |
| CN5 | Putative receptor protein kinase | 5e−29 |
| CN7 | Phagocytosis and cell mobility protein ELMO-1 related | 2e−82 |
| CN11 | Expressed protein | 3e−13 |
| CN13 | Putative forming-like protein AHF1 | 3e−54 |
| CN15 | Starch branching enzyme | 1e−78 |
| CC29 | Lipase-like protein | 1e−50 |
| CC39 | Putative receptor protein kinase | 1e−37 |
| CC40 | Putative chaperonin gamma chain | 5e−39 |
| CC48 | Expressed protein surface antigen ariel1-related | 1e−48 |
| CC50 | Type II metacaspase | 3e−61 |

[1]The ID of each clone starts with the name of the bait from which screen they obtained.

TABLE 3

The nucleotide sequences of primers used for developing baits for yeast two-hybrid screens

| Sequence to be amplified | Primer Name | Sequences |
|---|---|---|
| ORF | Rps1k1ORFF | CGC*GGATCC*GTATGGCAGCAGCACTGGTCGGT |
| | RpS1k2ORFR | GCCG*CTCGAG*CTAAATCCATCTATTGCCAAC |
| CC | Rps1k2ORFF | CGC*GGATCC*GTATGGCAGCAGCACTGGTCGGT |
| | Rps1k23CCR | GCCG*CTCGAG*CCATGACAAGTTCTCCACTGC |
| NB | Rps1k23NBSF | CGC*GGATCC*GTAAAGCTCCATCAACATCTCTG |
| | Rps1k2NBSR | GCCG*CTCGAG*TGATGTGGCTAGATCATGC |
| LRR | Rps1k23LRRF | CGC*GGATCC*GTTCGAAGCTTATGTACTTGAG |
| | Rps1k2ORFR | GCCG*CTCGAG*CTAAATCCATCTATTGCCAAC |
| CC-NB | RpS1k2ORFF | CGC*GGATCC*GTATGGCAGCAGCACTGGTCGGT |
| | Rps1k2NBSR | GCCG*CTCGAG*TGATGTGGCTAGATCATGC |
| NB-LRR | Rps1k23NBSF | CGC*GGATCC*GTAAAGCTCCATCAACATCTCTG |
| | Rps1k2ORFR | GCCG*CTCGAG*CTAAATCCATCTATTGCCAAC |

BamHI and XhoI recognition sites are in italics and underlined.

TABLE 4

The nucleotide sequences of primers used in pull down assay

| Target Sequence | Primer Name | Sequences |
|---|---|---|
| Individual cDNA | T7Kozak | CGAATTCTAATACGACTCACTATAGGGAACAGCCACCATGG |
| | KozakB42ADHA | GGAACAGCCACCATGGCCTCCTACCCTTATGATG |
| | B42ADdT$_{(30)}$ | TTTTTTTTTTTTTTTTTTTTTTTTTTTTTTGGCAAGGTAGACAAGC |

TABLE 4-continued

The nucleotide sequences of primers used in pull down assay

| Target Sequence | Primer Name | Sequences |
|---|---|---|
| Flag-tagged CC | T7Kozak | CGAATTCTAATACGACTCACTATAGGGAACAGCCACCATGG |
| | KozakFlag | CTTGTCATCGTCGTCCTTGTAGTCCATGGTGGCTGTTCC |
| | Rps1-kCCFlagF | GGACGACGATGACAAGGCAGCAGCACTGGTCGGTG |
| | Rps1-kCCdTR | GCCTGCAGTGAGATCCGCTACCATGACAAGTTCTCCAC |
| | SpOligodT | TTTTTTTTTTTTTTTTTTTTTTTTTTGCCTGCAGTGAGATCCG |
| Flag-tagged NB | T7Kozak | CGAATTCTAATACGACTCACTATAGGGAACAGCCACCATGG |
| | KozakFlag | CTTGTCATCGTCGTCCTTGTAGTCCATGGTGGCTGTTCC |
| | Rps1-kNBSFlagF | GGACGACGATGACAAGAAAGCTCCATCAACATCTC |
| | Rps1-kNBSdTR | GCCTGCAGTGAGATCCGCTATGATGTGGCTAGATCATG |
| | SpOligodT | TTTTTTTTTTTTTTTTTTTTTTTTTTGCCTGCAGTGAGATCCG |
| Flag-tagged CC-NB | T7Kozak | CGAATTCTAATACGACTCACTATAGGGAACAGCCACCATGG |
| | KozakFlag | CTTGTCATCGTCGTCCTTGTAGTCCATGGTGGCTGTTCC |
| | Rps1-kCCFlagF | GGACGACGATGACAAGGCAGCAGCACTGGTCGGTG |
| | Rps1-kNBSdTR | GCCTGCAGTGAGATCCGCTATGATGTGGCTAGATCATG |
| | SpOligodT | TTTTTTTTTTTTTTTTTTTTTTTTTTGCCTGCAGTGAGATCCG |

TABLE 5

The nucleotide sequences of primers used in RNAi experiment

| Target sequence | Primer Name | Oligo Sequence |
|---|---|---|
| RIP1 | RNAiNBS1F | 5'-GC*TCTAGA*CTCGAGAGGTGATAGCAGCAACAAAC-3' XbaI XhoI |
| | RNAiNBS1R | 5'-CC*ATCGAT*GGTACCACGATGATTCCAGTATGCTG-3' ClaI KpnI |
| RIP2 | RNAiNBS51F | 5'-GC*TCTAGA*gaattcCCAAGCTTCCTGATTCTGTTG-3' XbaI EcoRI |
| | RNAiNBS51R | 5'-CC*ATCGAT*GGTACCCATGTCATGAGGCATCTTTGC-3' ClaI KpnI |
| RIP3 | RNAiCN1F | 5'-GC*TCTAGA*CTCGAGCAACTGCAGAAGAATTCCTGC-3' XbaI XhoI |
| | RNAiCN1R | 5'-CC*ATCGAT*GGTACCCCATATGCTACATGTGATTCAC-3' ClaI KpnI |
| RIP4 | RNAiCN5F | 5'-GC*TCTAGA*CTCGAGCTATGACCTTCAATCGATGTG-3' XbaI XhoI |
| | RNAiCN5R | 5'-CCC*AAGCTT*GGTACCATCAGTGCTTGCAAAGGCAG-3' HindIII KpnI |
| RIP5 | RNAiCN7F | 5'-GC*TCTAGA*CTCGAGGAGCTTCCTTCACTTAAATC-3' XbaI XhoI |
| | RNAiCN7R | 5'-CC*ATCGAT*GGTACCCTCAACATGTTGTAAGCAGG-3' ClaI KpnI |
| RIP6 | RNAiCN11F | 5'-GC*TCTAGA*CTCGAGATCATACCCACATTCCTCAG-3' XbaI XhoI |
| | RNAiCN11R | 5'-CC*ATCGAT*GGTACCCATCAACCTCCAAACTTTGTC-3' ClaI KpnI |
| RIP7 | RNAiCN13F | 5'-GC*TCTAGA*CTCGAGCAGCTATGGATTCTGAAGTTC-3' XbaI XhoI |
| | RNAiCN13R | 5'-CC*ATCGAT*GGTACCCATGCAAGCTCTGACCAATC-3' ClaI KpnI |
| RIP9 | RNAiCC29F | 5'-GC*TCTAGA*CTCGAGACCGAAGCATAAGTTAGTTCC-3' XbaI XhoI |
| | RNAiCC29R | 5'-CC*ATCGAT*GGTACCATCTTTTGAATCCAGAGAGC-3' ClaI KpnI |
| RIP10 | RNAiC39F | 5'-GC*TCTAGA*CTCGAGCACATTGAGAGTGGAGATATAC-3' XbaI XhoI |
| | RNAiCC39R | 5'-CCC*AAGCTT*GGTACCCAATGTATCAGTGCTTGCAAAG-3' HindIII KpnI |
| RIP11 | RNAiCC40F | 5'-GC*TCTAGA*CTCGAGGATGGAAATACTGGCAGTATC-3' XbaI XhoI |

TABLE 5-continued

The nucleotide sequences of primers used in RNAi experiment

| Target sequence | Primer Name | Oligo Sequence |
|---|---|---|
|  | RNAiCC40R | 5'-CC*ATCGAT*GGTACCCATACGCCAGTTAATTAAGTC-3'<br>ClaI KpnI |
| RIP12 | RNAiCC48F | 5'-GC*TCTAGA*CTCGAGGCAGTAGAGCAGTTCCTAAC-3'<br>XbaI XhoI |
|  | RNAiCC48R | 5'-CC*ATCGAT*GGTAC*C*GACAAGCTAGTGTCACCATC-3'<br>ClaI KpnI |
| RIP13 | RNAiCC50F | 5'-GC*TCTAGA*CTCGA*G*TGGAGCTAAGGAGCAGATAG-3'<br>XbaI XhoI |
|  | RNAiCC50R | 5'-CC*ATCGAT*GGTAC*C*ACCACCATCATCACTTGAATC-3'<br>ClaI KpnI |

Example 2

We investigated (i) the nature of interactions between Rps1-k-2 and GmMcII (RIP13); (ii) steady state GmMcII protein levels following *Phytophthora sojae* infection. Results are briefly summarized below.

(i) The Nature of Interactions Between Rps1-k-2 and GmMcII

To confirm the in vivo interaction between GmMcII and Rps1-k-2-CC in etiolated soybean hypocotyls, the fluorescence resonance energy transfer (FRET) technology was applied. In FRET, the transfer of energy from one excited donor fluophore to an acceptor fluophore indicates the extent of closeness between the two molecules. FRET can occur if the donor and acceptor fluophore pair is in a favorable orientation and in close proximity (in general <7 nm). FRET can be observed by exciting the sample at the donor excitation wavelength while measuring the fluorescence intensity at the acceptor emission wavelength (Truong and Ikura, 2001). The commonly used fluophor pair are cyan fluorescent protein (CFP) as the donor and yellow fluorescent protein (YFP) as the acceptor. We constructed two plasmids; GmMcII was fused at the C terminus of the ECFP protein, while Rps1-k-2-CC was added in frame to the C terminus of the EYFP protein. Both fusion proteins were transiently expressed in etiolated soybean hypocotyls by particle bombardment. As shown in FIG. 9, when the EYFP-Rps1-k-CC fusion protein was expressed, bright signal was observed only in the YFP channel, but not in the CFP and FRET channels. Similarly, not much fluorescence was observed in the FRET channel when only the ECFP-CC50 fusion protein was expressed. When both ECFP and EYFP fusion proteins were co-expressed in the same cell, an increased fluorescence signal was detected in the FRET channel, as compared to the background signals (bleed-through) observed from expression of individual fusion proteins or the empty vector pair. These results suggested that CC50 interacted in vivo with Rps1-k-2-CC.

The pLexA yeast two-hybrid system (BD Biosciences Clontech, CA) was applied in determining the interacting domains of Rps1-k-2 and GmMcII. In addition to GmMcII, peptidases P20 and P10, and CC50 containing P10 and portion of P20 were considered for the interaction study. These four proteins were fused in frame to the activation domain of the pB42AD vector and four prey plasmids were obtained. Six bait plasmids CC, CN(CC-NBS), NBS, NBS-LRR, ORF (Rps1-k-2) and LRR (presented in FIG. 1), were transformed individually into yeast in combinations with individual prey plasmids for determining the interacting domains of Rps1-k-2 and GmMcII. Four colonies from each transformation combination were randomly selected for conducting four individual experiments. Comparable results were observed in all four experiments. Results of one of the four experiments are presented in FIG. 10. As shown in the figure, P10 and CC50 containing P10 interacted strongly with the CC domain of Rps1-k-2. Six bait plasmids are: CC, coiled-coil domain; NBS, nucleotide binding sites; LRR; leucine-rich repeat containing domain; CC-NBS, CC and NBS; NBS-LRR, NBS and LRR; Rps1-k-2, complete open reading frame. Four prey plasmids include: GmMcII, complete ORF of the metacaspase II; P20, N-terminal peptidase; P10, C-terminal peptidase; and partial GmMcII lacking the N-terminal region (original cDNA clone identified through yeast two-hybrid screening using CC domain as the bait. Yeast strain EGY48 containing the reporter plasmid, pSH18-34 was double transformed with corresponding prey and bait plasmids and grown on 5-bromo-4-chloro-3-indolyl-β-D-galactopyranoside (X-gal) plates lacking tryptophan, histidine and uracil (A) or on plates lacking tryptophan, histidine, uracil and leucine (B).

Expression of β-galactosidase as shown by blue color development in A was recorded for all combinations of CC with four prey plasmids. This observation suggests strong interactions of CC with P10 and partial GmMcII containing P10 (FIG. 10). We observed 17% amino acid identity and 38% similarities between P20 and P10 domains and extensive similarities between the secondary structures of P20 and P10 peptidases (bioinf.cs.ucl.ac.uk/psipred/psiform.html) and structures of P10 and P20 are presumable distinct for binding to CC domain of Rps1-k-2. Growth on the plate lacking leucine (B) suggested that there were poor interactions of GmMcII and its peptidases with CC, CC-NBS, and NBS but not with NBS-LRR, LRR and Rps1-k-2.

(ii) Steady state GmMcII protein levels following *Phytophthora sojae* infection: We conducted western blot analyses of the etiolated soybean hypocotyl tissues infected with *P. sojae* for investigating the status of GmMcII levels. Etiolated hypocotyls either infected with *P. sojae* zoospores or treated with water droplets. As shown in FIG. 11, two strong protein bands hybridized to the anti-mcII-Pa antibody raised against the Norway Spruce mcII, kindly provided by Dr. Peter V. Bozhkov. These bands were processed within two hours following infection.

FIG. 11 shows GmMcII is processed in infected hypocotyl tissues. Etiolated hypocotyls of 7-day old seedlings were inoculated with *P. sojae* zoospore or $H_2O$ droplets, and thin tissue sections just beneath the zoospore or water droplets were excised two hours following infection or $H_2O$ droplet treatment. Tissues were immediately frozen in liquid $N_2$ and processed for western blotting using the anti-mcII-Pa antibody. 1, Williams treated with H₂0 droplets; 2, Williams 82 treated with H₂0 droplets; 3, Williams infected with *P. sojae;* 4, Williams 82 infected with *P. sojae* zoospores. Williams produced susceptible response and Williams 82 produced resistant response following infection with *P. sojae*. Note that two protein bands, strongly hybridized to the antibody in water controls (lanes 1 and 2), were processed following infection (Lanes 3 and 4). Anti-mcII-Pa antibody hybridized to the *E. coli*-expressed GmMcII protein (data not shown).

Data presented in FIG. 11 suggested GmMcII is processed in both compatible and incompatible interactions. Further study will be required if there are any variations in processing of the enzyme(s) in the two interactions.

---

What is claimed is:

1. A modified soybean plant with improved *Phytophthora* tolerance compared to the *Phytophthora* tolerance of a corresponding plant with no such modification; the improved *Phytophthora* tolerance being due to modulated metacaspase activity in said plant, said plant having stably incorporated in its genome a nucleic acid molecule, said molecule encoding a *Phytophthora*-responsive protein wherein said nucleic acid molecule comprises:

(a) a nucleotide sequence comprising the sequence set forth in SEQ ID NO: 1; and (b) a nucleotide sequence having at least 95% sequence identity to SEQ ID NO:1 wherein said nucleotide sequence encodes a protein for phytophthora resistance.

2. The plant of claim 1 wherein said modulation is an increased amount of a metacaspase protein.

3. The plant of claim 1 wherein said metacaspase protein is metacaspase type II.

4. The plant of claim 1 wherein said modulation is an increased activity of metacaspase protein in said plant.

5. The plant of claim 1 wherein said metacaspase modulation includes an increased interaction with Rps1-k-2 or coiled-coil domain of Rps1-k-2 or any other plant proteins.

6. A soybean plant cell having stably incorporated in its genome a nucleic acid molecule, said molecule encoding a Phtyophthora-responsive protein wherein said nucleic acid molecule comprises a nucleotide sequence:

(a) comprising the sequence set forth in SEQ ID NO: 1; and (b) a nucleotide sequence having at least 95% sequence identity to SEQ ID NO:1 wherein said nucleotide sequence encodes a protein for phytophthora resistance.

7. A method for conferring or improving *Phytophthora* resistance in a plant, said method comprising:

transforming said plant with a nucleic acid molecule comprising a heterologous sequence operably linked to a promoter that induces transcription of said heterologous sequence in a plant cell in response to a *Phytophthora* stimulus; and regenerating stably transformed plants, wherein said heterologous sequence comprises a nucleotide sequence selected from the group consisting of:

(a) a nucleotide sequence comprising the sequence set forth in SEQ ID NO: 1;

(b) a nucleotide sequence having at least 95% sequence identity to the sequence of SEQ ID NO: 1.

8. The method of 7, wherein said plant is a dicot.

9. The method of 7, wherein said dicot is soybean.

10. An isolated nucleic acid molecule operably linked to a promoter that drives expression in a host cell, said nucleic acid molecule encoding a polypeptide having metacaspase type II-like activity, said nucleic acid molecule being selected from the group consisting of:

(a) a nucleic acid molecule comprising the sequence set forth in SEQ ID NO: 1;

(b) a nucleic acid molecule comprising a sequence encoding the amino acid sequence set forth in SEQ ID NO: 2;

(c) a nucleic acid molecule comprising a full length complement corresponding to the sequence of a), or b); and (d) a nucleic acid molecule comprising a sequence having at least 95% sequence identity to the nucleotide sequence set forth in SEQ ID NO: 1.

11. The nucleic acid molecule of claim 10 wherein said molecule is a soybean nucleic acid.

12. A cell having stably incorporated into its genome at least one nucleotide construct comprising:

a nucleic acid molecule operably linked to a heterologous promoter that drives expression in said cell, wherein said nucleic acid molecule encodes a polypeptide having metacaspase II-like activity and is selected from the group consisting of:

(a) a nucleic acid molecule comprising the sequence set forth in SEQ ID NO: 1;

(b) a nucleic acid molecule comprising a sequence encoding the amino acid sequence set forth in SEQ ID NO: 2;

(c) a nucleic acid molecule comprising a full length complement corresponding to the sequence of a), or b); and (d) a nucleic acid molecule comprising a sequence having at least 95% sequence identity to the nucleotide sequence set forth in SEQ ID NO: 1.

13. The cell of claim 12, wherein said cell is a plant cell.

14. A transformed plant having stably incorporated into its genome at least one nucleotide construct comprising:

a nucleic acid molecule operably linked to a heterologous promoter that drives expression in a plant cell, wherein said nucleic acid molecule encodes a polypeptide having metacaspase-like activity and is selected from the group consisting of:

(a) a nucleic acid molecule comprising the sequence set forth in SEQ ID NO: 1;

(b) a nucleic acid molecule comprising a sequence encoding the amino acid sequence set forth in SEQ ID NO: 2;

(c) a nucleic acid molecule comprising a full length complement corresponding to the sequence of a), or b); and (d) a nucleic acid molecule comprising a sequence having at least 95% sequence identity to the nucleotide sequence set forth in SEQ ID NO: 1.

15. The plant of claim 14, wherein said promoter is a constitutive promoter.

16. The plant of claim 14, wherein said promoter is a tissue-preferred promoter.

17. The plant of claim 14, wherein said promoter is an inducible promoter.

18. The plant of claim 14, wherein said plant is a dicot.

19. The plant of claim 14, wherein said dicot is soybean.

20. Transformed seed of the plant of claim 14.

21. The plant of claim 2 wherein said metacaspase protein is a polypeptide comprising the amino acid sequence set forth in SEQ ID NO: 2.

* * * * *